United States Patent [19]

Chao

[11] Patent Number: 5,771,269
[45] Date of Patent: Jun. 23, 1998

[54] APPARATUS AND METHOD FOR REMOVING SCATTER FROM AN X-RAY IMAGE

[75] Inventor: Yong-Sheng Chao, Storrs, Conn.

[73] Assignee: Advanced Optical Technologies, Inc., E. Hartford, Conn.

[21] Appl. No.: 725,375

[22] Filed: Oct. 3, 1996

Related U.S. Application Data

[63] Continuation-in-part of Ser. No. 580,602, Dec. 29, 1995, Pat. No. 5,648,997.

[51] Int. Cl.⁶ .............................. G21K 1/12; G21K 5/10
[52] U.S. Cl. ............................. 378/5; 378/147; 378/901
[58] Field of Search .......................... 378/62, 147, 901, 378/4, 5

[56] References Cited

U.S. PATENT DOCUMENTS 5,148,455   9/1992   Stein ........................................ 378/55

OTHER PUBLICATIONS

Lehmann et al., *Generalized Image Combinations in Dual KVP Digital Radiography*, 8 Medical Physics 659 (Sep./Oct. 1981).

Archer et al., *A Laplace Transform Pair Model for Spectral Reconstruction*, 9 Medical Physics 844 (Nov./Dec. 1982).

Wahner et al., *The Evaluation of Osteoporosis: Dual Energy X-Ray Absorptiometry in Clinical Practice*, 14–33 (1994) no month.

Lo et al., *Scatter Compensation in Digital Chest Radiography Using the Posterior Beam Stop Technique*, 21 Medical Physics 435 ( Mar. 1994).

Lee et al., *A New Digital Detector for Projection Radiography*, SPIE (Feb. 1995).

Petrone et al., *Rare-Earth Scatter Fractions in Chest Radiography*, 20 Medical Physics 475 (Mar./Apr. 1993).

Zhao et al., *Digital Radiology Using Self-Scanned Readout of Amorphous Selenium*, 1896 SPIE Physics of Medical Imaging 114 (1993) no month.

Antonuk et al., *Demostration of Megavoltage and Diagnostic X-Ray Imaging with Hydrogenated Amorphous Silicon Arrays*, 19 Medical Physics 1455 (Nov./Dec. 1992).

Honda et al., *A Technique of Scatter-Glare Correction Using Digital Filtration*, 20 Medical Physics 59 (Jan./Feb. 1993).

Floyd et al., *Quantitative Scatter Measurement in Digital Radiography Using Photostimulable Phosphor Imaging System*, 18 Medical Physics 408 (May./Jun. 1991).

(List continued on next page.)

*Primary Examiner*—Don Wong
*Attorney, Agent, or Firm*—Morse, Altman & Benson

[57] ABSTRACT

Apparatus and method for eliminating scatter effects in x-ray imaging using two-dimensional detector arrays. The apparatus consists of, in physical order, an x-ray source, a front two-dimensional x-ray detector, a beam selector, and a rear two-dimensional x-ray detector. The subject is located between the x-ray source and front detector. The beam selector prevents scatter x-rays from reaching the rear detector. The method simultaneously solves the two interdependent problems of obtaining scatter-free x-ray images and conducting dual-energy x-ray imaging with primary x-ray data. A high-resolution composite image containing primary and scatter x-ray components is read from the front detector. A low-resolution composite image is produced from the high-resolution composite image. A pair of low-resolution primary x-ray dual-energy images is read from the rear detector. Using an improved dual-energy data decomposition method, a low-resolution primary x-ray front detector image is calculated. A low-resolution scatter x-ray image is determined by subtracting the low-resolution primary x-ray front detector image from the low-resolution composite image. The low-resolution scatter x-ray image is interpolated to a high-resolution scatter x-ray image and subtracted from the high-resolution composite image to produce a high-resolution primary x-ray image.

41 Claims, 12 Drawing Sheets

OTHER PUBLICATIONS

Zhao et al., *A Large Area Solid–State Detector for Radiology Using Amorphous Selenium*, 1651 SPIE Medical Imaging IV: Instrumentation 134 (1992) no month.

Chan et al., *Studies of Performance of Antiscatter Grids in Digital Radiography: Effects on Signal–to–Noise Ratio*, 17 Medical Physics 655 (Jul./Aug. 1990).

Honda et al., *Method for Estimating the Intensity of Scattered Radiation Using a Scatter Generation Model*, 18 Medical Physics 219 (Mar./Apr. 1991).

Archer et al., *Laplace Reconstruction of Experimental Diagnostic X–Ray Spectra*, 15 Medical Physics 732 (Nov./Dec. 1988).

Cardinal et al., *An Accurate Method for Direct Dual–Energy Calibration and Decomposition*, 17 Medical Physics 327 (May/Jun. 1990).

Boone et al., *An Analytical Model of the Scattered Radiation Distribution in Diagnostic Radiology*, 15 Medical Physics 721 (Sep./Oct. 1988).

Wagner et al., *Dual–Energy X–Ray Projection Imaging: Two Sampling Schemes for the Correction of Scattered Radiation*, 15 Medical Physics 732 (Sep./Oct. 1988).

Vetter et al., *Correction for Scattered Radiation and Other Background Signals in Dual–Energy Computed Tomography Material Thickness Measurements*, 15 Medical Physics 726 (Sep./Oct. 1988).

Speller et al., *Monte Carlo Study of Multiple Scatter Effects in Compton Scatter Sitometry*, 15 Medical Physics 707 (Sep./Oct. 1988).

Boone et al., *Monte Carlo Simulation of the Scattered Radiation Distribution in Diagnostic Radiology*, 15 Medical Physics 713 (Sep./Oct. 1988).

Chuang et al., *Comparison of Four Dual Energy Image Deconstruction Methods*, 4 Physics in Medicine and Biology 455 (1988) no month.

Seibert et al., *X–Ray Scatter Removal by Deconvolution*, 15 Medical Physics 567 (Jul./ Aug. 1988).

APPARATUS AND METHOD FOR REMOVING SCATTER FROM AN X-RAY IMAGE

RELATED APPLICATIONS

The present application is a continuation-in-part application of application Ser. No. 08/580,602, dated Dec. 29, 1995, U.S. Pat. No. 5,648,997, for APPARATUS AND METHOD FOR REMOVING SCATTER FROM AN X-RAY IMAGE in the name of Yong-Sheng Chao.

GOVERNMENT FUNDING

The research involved in this application was funded in part by the National Aeronautics and Space Administration, contract number NAS 9-19061. The intellectual property rights of the applicant and the government of the United States of America are governed by Title 37 Code of Federal Regulations Part 401.

BACKGROUND OF THE INVENTION

1. Field of the Invention

This invention relates generally to digital x-ray imaging and, more particularly, relates to methods and apparatuses for reducing scatter in two-dimensional x-ray imaging and two-dimensional dual-energy x-ray imaging.

The Prior Art Recent advances in the field of semiconductor fabrication have resulted in the ability to fabricate large-format two-dimensional integrated detector arrays for x-ray detection. These arrays have on the order of one million detector cells and provide instant acquisition of two-dimensional x-ray images with exceedingly high quality.

Scatter, which results from those x-rays that strike objects and deflect in random directions, has been a difficult and on-going problem in x-ray imaging using two-dimensional detectors. For example, in projection chest radiography, scatter typically accounts for between approximately 30% and 50% of the total amount of x-rays detected.

With single-point detectors or linear detector arrays, because of the inherent geometric configuration of the detector, scatter can be controlled to a negligible level. However, two-dimensional detectors are exposed to wide-angle random scatter. Randomly scattered x-rays are superimposed on the primary x-rays (the x-rays coming directly from the x-ray source) and recorded by two-dimensional detectors undifferentiated, degrading the true image. Scatter tends to reduce image contrast, produce blurring, and reduce signal-to-noise ratio. Furthermore, if scatter is not substantially reduced, almost all quantitative diagnostic x-ray imaging using two-dimensional detector arrays becomes meaningless. For example, currently, dual-energy x-ray imaging, which is a method for determining two material composition images of a subject, has been limited to only using point or linear detector array scanning to gain a two-dimensional image. Because of scatter, dual-energy x-ray imaging has been unable to use two-dimensional detectors.

Another example is three-dimensional x-ray imaging. It is well-known that three-dimensional tomographic image reconstruction is inherently very sensitive to the error contained in its two-dimensional projection images used as input data. With scatter present, three-dimensional image reconstruction becomes meaningless. Because of this, large format two-dimensional x-ray detectors have not been available for use in medical three-dimensional diagnostic x-ray imaging. Thus, unless scatter is substantially removed or eliminated, two-dimensional detector arrays cannot be used in dual-energy x-ray imaging, three-dimensional diagnostic x-ray imaging, or in other quantitative imaging modalities.

The present invention uses the dual-energy x-ray imaging method as a foundation for the method of eliminating scatter. However, the dual-energy x-ray imaging methods of prior art are not suitable for this purpose.

According to current theory and empirically derived data, a large number of complex material systems can be decomposed into only two basis material compositions in terms of x-ray absorption. In the case of the human body, these two materials are often taken as bone tissue and soft tissue, abbreviated b and s, respectively. In the remainder of this disclosure, the phrase "two materials" is used to indicate the two basis materials. In the field of dual-energy x-ray imaging, the phrases "two materials" and "two basis materials" are used interchangeably without confusion. The prior art of dual-energy x-ray data decomposition methods is summarized in Keh-Shih Chung & H. K. Huang, Comparison of Four Dual-energy Image Decomposition Methods, 4 Physics in Medicine and Biology 455 (1988), and in the book Heinz W. Wahner & Ignac Fogelman, The Evaluation of Osteoporosis: Dual-energy X-ray Absorptiometry in Clinical Practice 14–33 (1994). All the dual-energy x-ray data decomposition methods of the prior art have a common approach. They all use two single-energy values to replace the broad bremsstrahlung spectra of x-ray energy : the average energy $E_H$ for the high-energy x-rays and the average energy $E_L$ for the low-energy x-rays. Thus, the dual-energy equations are greatly simplified into a pair of linear algebraic equations that can be readily solved for b and s:

$$L_H = \ln(I_H/I_{HO}) = -(\mu_b(E_H) \times b + \mu_s(E_H) \times s) \quad (1a)$$

$$L_L = \ln(I_L/I_{LO}) = -(\mu_b(E_L) \times b + \mu_s(E_L) \times s) \quad (1b)$$

where $I_{HO}$ and $I_{LO}$ are the incident x-ray beam intensities at energies $E_H$ and $E_L$, respectively, $I_H$ and $I_L$ are the measured signals read from high-energy and low-energy detectors, respectively, $\mu_b(E_H)$ and $\mu_b(E_L)$ are the mass absorption coefficients of bone tissue of high-energy and low energy x-rays, respectively, and $\mu_s(E_H)$ and $\mu_s(E_L)$ are the mass absorption coefficients of soft tissue of high-energy and low energy x-rays, respectively. In the art, $\mu$ is also referred to as the mass attentuation coefficient. Thus, b and s can be analytically determined as simple functions of experimental data $L_H$ and $L_L$.

The linearized results are subjected to numerous correction methods, including extending to a second order of b and s values. These different correction methods account for the various data decomposition methods of the prior art. As described in above quoted publications, it is a consensus that the dual-energy x-ray data decomposition methods of the prior art can only work with linear or point detectors for small pixel number imaging, because these methods require the user to make frequent judgments in the course of data decomposition; hence none of these methods is suitable for use with million-pixel two-dimensional detector arrays, where the data decomposition must be carried out automatically by computers without user intervention. There are at least two specific problems with the dual-energy data decomposition methods of the prior art. The first problem is that the average energy value EH or EL varies in a too wide range for human body imaging. The average energy values assigned by the user based on certain judgments inevitably introduce a great deal of arbitrariness leading to substantial error. The second important problem is that the linear and second order methods cannot generally ensure that the correct results can always be obtained through a defined procedure. For example, for the correction of "beam hardening effects", linear methods often require additional data regarding human body thickness. This is not always practical. For the second order approximation methods, there has been no guarantee that a unique solution of the quadratic equation system always exists.

One object of the invention is to provide a substantially improved dual-energy x-ray imaging method so that the data decomposition can be completely carried out by computer, and a unique, rigorous, and accurate solution of the dual-energy equation system can always be obtained.

Currently, there are two basic methods for reducing scatter in two-dimensional x-ray imaging. The first method uses an anti-scatter grid or improved grid devices to slightly relieve scatter effects on images. An anti-scatter grid consists of large number of fine wires placed in front of the detector. Because the grid has a certain amount of collimating ability, the randomly scattered x-rays can be somewhat reduced. However, the grid also tends to attenuate the primary x-rays, causing distortion of the primary image. Thus, the grid must be thin, limiting its ability to reduce scatter. Recent research results show that up to about 50% of the scatter radiation can be reduced through use of an anti-scattering grid. By increasing the air gap between the subject and the detector, the scatter can also be reduced, but at the same time, the image is blurred due to the geometric distance the x-rays have to travel.

The second method to reduce scatter is to calculate theoretical estimates of the amount of scatter and subtract these estimates from the detected image. Theoretical calculation methods, including Monte Carlo simulation methods and analytical deconvolution methods, can only give crude predictions, because these methods cannot calculate the variation of scatter due to individual features of image subjects.

The object of the present invention is to provide apparatus and method to produce scatter-free dual-energy x-ray images and to accurately remove scatter effects from images detected by two-dimensional x-ray detector arrays. When the scatter is thus effectively eliminated, two-dimensional detectors gain new uses in dual-energy x-ray imaging, three-dimensional diagnostic x-ray imaging, and other quantitative x-ray imaging modalities.

SUMMARY OF THE INVENTION

The basic methods of the present invention include a method for dual-energy x-ray data decomposition and a method for eliminating scatter.

The dual-energy x-ray data decomposition method in this invention is part of the method for eliminating scatter. The dual-energy x-ray data decomposition method of the present invention directly solves the nonlinear dual-energy x-ray imaging fundamental equation system in its original form without relying on any linear or second order approximations. The method includes: (1) Constructing an explicit quantitative equation system $D_H=D_H(b,s)$ and $D_L=D_L(b,s)$ for each detector according to the nonlinear dual-energy x-ray imaging fundamental equation system in its original form and saving them for later use, where $D_H$ represents the high-energy primary x-ray signal and $D_L$ represents the low-energy primary x-rays signal. The dual-energy x-ray imaging fundamental equation system in its original form does not contain any linearization approximations nor any series expansion processes. (2) reconstructing a three-dimensional surface equation system $b=b(D_H,D_L)$ and $s=s(D_H,D_L)$ by numerically inverting the equation system of step 1 and saving them for later use. (3) Determining the desired values for b and s at each discrete detector cell location by inserting the available data pair $(D_H,D_L)$ into the numerical equations of step 2, or determining the desired values for $D_H,D_L$, or only one of them, at each discrete detector cell location by inserting the available data pair (b,s) into the numerical equations of step 1. (4) Maintaining the accuracy at each step to be as high as real number analytical solutions can provide.

The essential part of the apparatus of the present invention for eliminating scatter is an x-ray detection system that directly detects primary x-rays without scatter at a number of selected locations in addition to detecting conventional images. The most important specific features are as follows. (1) The present invention uses a beam selection means that physically and completely separates the primary x-rays from the scatter x-rays at a number of selected locations. (2) The present invention uses an x-ray detection system that has a multilayer structure: the beam selector is sandwiched between a front detector assembly and a rear detector assembly. The front detector assembly detects the primary and scatter x-rays, the rear detector assembly detects only the primary x-rays at selected locations without scatter. (3) The beam selector substantially blocks the scatter x-rays at a number of selected locations on the rear detector assembly, and the passage of the primary x-rays to these selected locations is not blocked. Blocking the scatter x-rays is defined as reducing the scatter x-ray signal at the rear detector to an insignificant quantity, for example, less than the noise signal of the rear detector. Because of the beam selector, the rear detector assembly receives only primary x-rays at these selected locations. Note that that it is important that scatter x-rays, not primary x-rays, are blocked; otherwise, no successful results would be achieved. Reasons for this will be given below. These three specific features are the most important difference in hardware between the present invention and prior art.

In terms of the method for eliminating scatter x-rays, the present invention provides a method for completely determining the high spatial resolution primary image of the front detector from the primary image data acquired by the rear detector assembly at the selected locations. More specifically, there are two important features. (1) The present invention uses a dual-energy method to determine the primary image of the front detector at the corresponding selected locations from the image data of the rear detector assembly. Note the crucial importance of using dual-energy method. Without using dual-energy method, the image of the front detector could not be uniquely determined, hence the scatter could not be eliminated. Reasons for this will be given below. (2) The present invention uses an interpolation method to extend the scatter component of the front detector image determined at a the selected locations to the entire image area of the front detector. Following this, a complete separation of scatter and primary images for the front detector at high spatial resolution is achieved.

Thus, an object of the present invention is to provide an apparatus and method for substantially eliminating the effects of scatter on two-dimensional x-ray detectors.

A further object of the present invention is to provide an apparatus and a method for scatter-free dual-energy x-ray imaging using two-dimensional detectors and to provide two high accuracy material composition images of a subject at the spatial resolution as high as a two-dimensional detector array can provide.

BRIEF DESCRIPTION OF THE DRAWINGS

For a fuller understanding of the nature and object of the present invention, reference is made to the accompanying drawings, wherein.

DETAILED DESCRIPTION

Introduction

The present invention comprises an apparatus and method for providing scatter-free dual-energy x-ray imaging using two-dimensional detectors. The basic apparatus includes five components: (1) an x-ray source, (2) a front two-dimensional x-ray detector assembly, (3) a beam selector, (4) a rear two-dimensional x-ray detector assembly, and (5) a computer.

Figure 1:
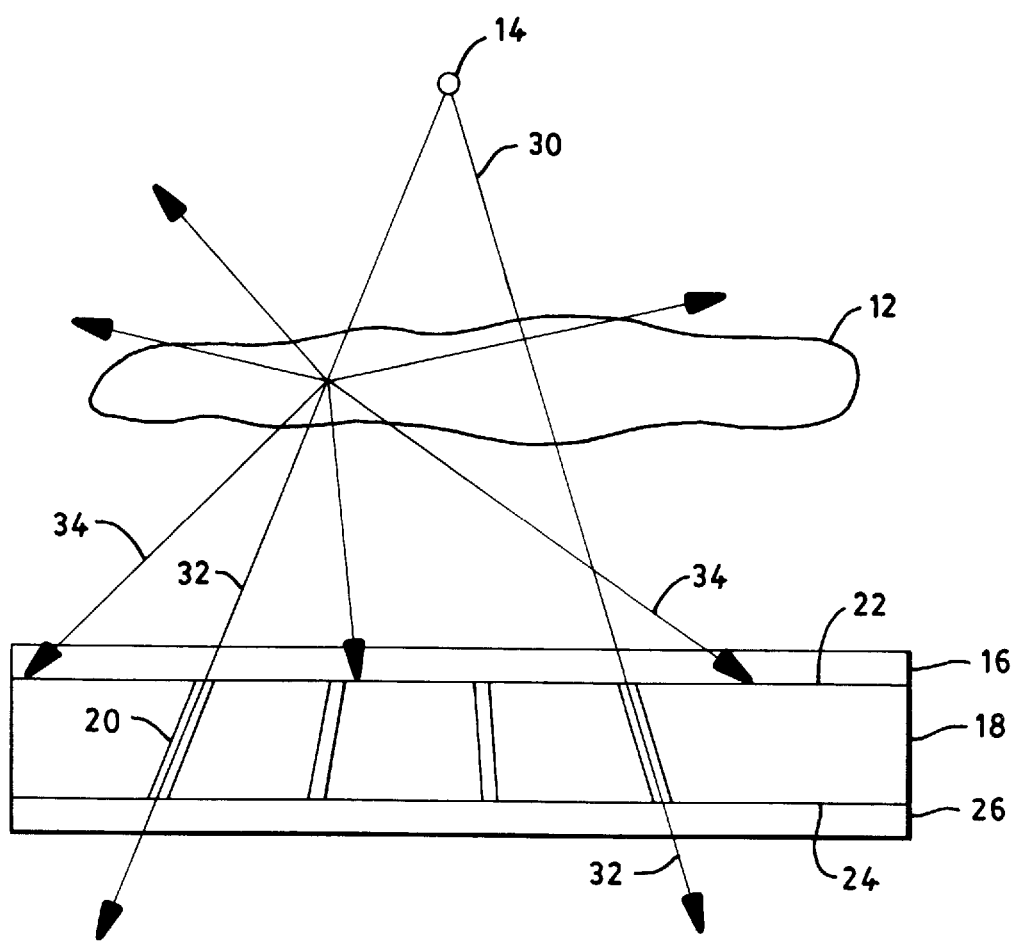
FIG. 1 is a diagram of the basic hardware of the present invention.
Figure 2:
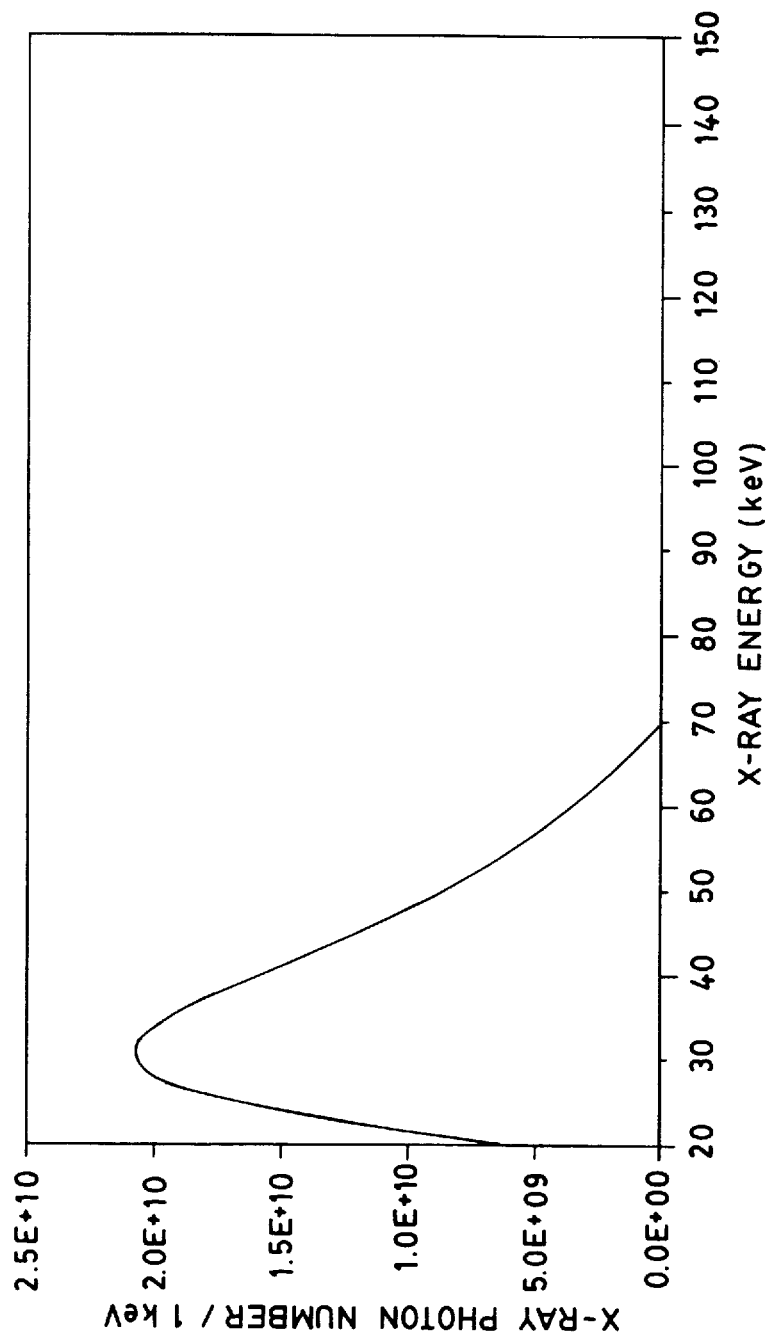
FIG. 2 is a curve describing a typical x-ray source energy spectrum used in the present invention.

As shown in FIG. 1, the subject under examination 12 is located between the x-ray source 14 and the front detector assembly 16. The x-ray source 14 emits x-rays 30, preferably with an energy in the range of from 10 keV to 500 keV, as shown in FIG. 2. The x-ray source 14 is essentially a point source, meaning that the x-rays appear to be emanating from a single point rather than from a larger area. A portion of the x-rays 32 passes through the subject 12 directly to the front detector assembly 16 without a change in their direction of propagation. These x-rays 32 are called the primary x-rays and convey true information about the subject 12. The remainder of the x-rays 34 are randomly scattered as a result of interaction with the material of the subject 12. These x-rays 34 are called scatter and cause a distortion of the true information.

The front detector in the front detector assembly 16 contains a large number of individual detector cells in a two-dimensional array. Although the present invention is not limited to a particular type of x-ray detector array, there are two basic types. The first uses thin film amorphous silicon as photodetection medium. The amorphous silicon film has a typical thickness of 1 micrometer ($\mu$m) and is sensitive to visible light. The electric charge induced by visible photons is collected by an array of electrodes. An scintillation screen, which is the x-ray sensitive medium, is placed in close contact with the entire photosensitive area of the photodetector array. X-rays cause the generation of visible photons in the scintillation screen, which are then detected by the amorphous silicon photodetector array, inducing an electric charge proportional to the x-ray energy absorbed in the screen. This type of x-ray detector array is called an external conversion type x-ray detector. Preferably, the detector array has dimensions of 20 centimeters (cm) by 20 cm or 40 cm by 40 cm for a single detector module. A number of such detector modules can be butted together to provide a larger detector. The cell size for this detector array is in the range of from approximately 50 $\mu$m by 50 $\mu$m to approximately 1 mm by 1 mm.

A second type of detector array uses an amorphous selenium film or selenium alloy film as the x-ray sensitive medium. The charge induced by x-rays directly in the selenium film is collected by an array of electrodes and is proportional to the energy of the x-rays striking the film. The typical thickness of the selenium film is in the range of from approximately 100 $\mu$m to approximately 800 $\mu$m. This type of x-ray detector array is called an internal conversion type x-ray detector. A typical amorphous selenium or selenium alloy detector array module has dimensions of 20 cm by 20 cm or 40 cm by 40 cm with a cell size of from approximately 50 $\mu$m by 50 $\mu$m to approximately 1mm by 1 mm. A number of such detector modules can be butted together to create a larger detector array.

Other typical two-dimensional detector arrays include charge-couple device (CCD) detectors, thin-film thalliumbromide-based detector arrays, avalanche silicon detector arrays, and phosphor-stimulatable computed radiography screens.

The cells of the front detector assembly 16 have variations in their response characteristics. However, these variations are slight and can be normalized, so it is assumed that after normalization, all detector cells in the detector have the same response characteristics.

The combination of signals from all of the cells conveys an image of the x-ray intensity over the area of the front detector assembly 16. Because the cells cannot distinguish between primary x-rays 32 and scatter 34, the front detector assembly 16 conveys an image that is a combination of the primary x-rays 32 and the scatter 34, and is denoted by $$D_{fh}(x,y)=D_{fPh}(x,y)+D_{fSh}(X,Y) \qquad (2)$$

where $D_f$ denotes an image in the front detector assembly 16 and (x,y) denotes the two-dimensional Cartesian coordinates of a cell of the front detector assembly 16. For example, when the front detector assembly 16 has a 1024-cell square matrix, x and y will each have integer values in the range of from 1 to 1024, inclusive. $D_{fPh}(x,y)$ denotes the contribution from the primary x-rays 32 and $D_{fSh}(X,Y)$ denotes the contribution from the scatter 34.

The present invention uses a beam selection means for physically separating primary x-rays from scatter x-rays. The beam selector is sandwiched between the front detector assembly 16 and the rear detector assembly 26, blocking substantially the passage of all said scatter x-rays 34 from the image subject to locations on the x-ray-sensitive medium of the rear detector assembly 26, and permitting the passage of the primary x-rays 32 to those locations. A preferred embodiment of the x-ray beam selector 18 is a quantity of x-ray-absorbent material having a large number of holes 20. The holes 20 are fabricated such that their axes are aligned with the travel direction of the primary x-rays 32. As a result, the holes 20 permit all x-rays traveling along the axes of the holes 20 to pass through, while all x-rays traveling in directions deviating slightly from the hole axes are completely absorbed by the bulk material of the beam selector 18. Thus, by using direction selection, only he primary x-rays 32 reach the x-ray sensitive medium of he rear detector assembly 26. Because the holes 20 always have a finite size, a small portion of randomly scattered x-rays from the image subject 12 still reach the rear detector assembly 26. However, as long as the hole size 20 is small and the thickness of the beam selector 18 is sufficiently large, this portion of the scatter 34 can be controlled to be negligibly small in comparison with other error sources, such as the error caused by statistical fluctuation of the x-ray photon number. The cross-sectional shape of the holes 20 is not important, but for ease in manufacturing, they are preferably round or square. The size of the beam selector holes 20 is generally much larger than the size of single detector cells. Preferably, the holes 20 are as small as possible, but for cost reasons, they have a diameter that is in the range of approximately from 0.5 mm to 10 mm. If the holes 20 are too large, they will not prevent all of the scatter 34 from reaching the x-ray-sensitive medium of the rear detector assembly 26. Preferably, there are as many holes as possible in the beam selector 18. The more holes 20 there are in the beam selector 18, the greater the accuracy of the measurement at the rear detector 26. In any case, the beam selector material must occupy enough area so that the amount of scatter 34 is reduced to an insignificant quantity. A compromise based on these factors results in a pitch that is preferably between 2 mm and 50 mm. The holes 20 are fabricated such that their axes are aligned with the direction of the travel of the primary x-rays 32, which means that, because the x-rays are emitted from essentially 5 a point source, the holes 20 are not exactly parallel to each other, but are radial to the x-ray source. As the x-ray source 14 is located farther away from the beam selector 18, the holes 20 approach being parallel to each other.

Preferably, the x-ray source 14 is located between 20 cm and 150 cm from the rear surface 24 of the beam selector 18. The invention holds equally true when the x-ray source has a finite size.

The material of the beam selector 18 must ensure that all scatter 34 is absorbed and that, except for the primary x-rays passing through the holes, none of the other radiations, including scatter and secondary emissions caused either by primary x-rays or by scatter, reaches the rear detector 26.

There may also be scatter x-rays from the sources other than the image subject 12, such as, for example, from the wall or floor of the building material. These scatter x-rays are excluded by using conventional methods.

The beam selector 18 has approximately the same area as the front detector 16 and is preferably between 0.5 cm and 10 cm in thickness. After exiting the beam selector 18, the x-rays strike the rear detector assembly 26, which works in the same way as the front detector assembly 16. Because of the action of the beam selector 18, the image recorded by the rear detector assembly 26 is only that of primary x-rays 32. Preferably, the rear detector cells are arranged in a rectangular matrix with from 8 to 1,024 cells on a side.

The term "selected location" is defined as the location on the x-ray sensitive medium of the rear detector assembly 28, or on a rear detector, where, due to the function of the beam selector, only primary x-rays are received, and the scatter x-rays are substantially blocked. The "selected projection line" is defined as a straight line connecting the x-ray source to a point in the "selected location". Usually the point is close to the center of the selected location. The "projection line" is defined as a line connecting the x-ray source to any point in the space. Note that for the rear detector assembly 26, only the signals at the selected locations are utilized. The rear detector cells at the selected locations have a fixed geometric relation with some of the front detector cells. This relation is established by drawing a selected projection line from the x-ray source 14 through the beam selector 18 to the selected location. This selected projection line intersects the rear detector surface at a rear detector cell at a coordinate (i,j), and intersects the front detector surface at a front detector cell at a coordinate $(x(i),y(j))$. Here $(x(i),y(j))$ denote the Cartesian coordinate $(x,y)$ of the front detector cell in the front detector assembly 16 closest to the selected projection line. An image file $D_{r1}(i,j)$ acquired from the rear detector assembly 26 contains only the signals at the selected locations where the primary x-rays are received, and the scatter x-rays are substantially blocked. The data at the image pixel (i,j) is the data obtained either from a single detector cell or from a combination of a small number of detector cells around the selected projection line. Similarly, $D_{fl}(x(i),y(j))$ denotes an image file from the front detector assembly 26 having a low spatial resolution. The data at the image pixel $(x(i),y(j))$ is the data either of a single detector cell or of a combination of a small number of detector cells around the selected projection line. The relationship between (i,j) and $(x(i),y(j))$ is experimentally established for all of the holes 20 of the beam selector 18 and stored. The images represented by the composite of the signals from the detector cells of only one detector on the selected projection lines are low-resolution images and are represented by the subscript lower-case 1. The images represented by the composite of the signals from all the front detector cells are high-resolution images and are represented by the subscript lower-case h.

In connection with the material composition of the image subject, four quantities are defined. b(i,j) and (i,j) are defined as the selected projection mass densities long the selected projection line (i,j). b(x,y) and s(x,y) are defined as the projection mass densities along the projection line (x,y). The "projection mass density" is defined as the integrated total mass of the image subject along the projection line per unit area. Because the projection mass density is not dependent on the size of detector cells, $b(x(i),y(j))=b(i,j)$ and $s(x(i),y(j))=s(i,j)$.

Figure 4:
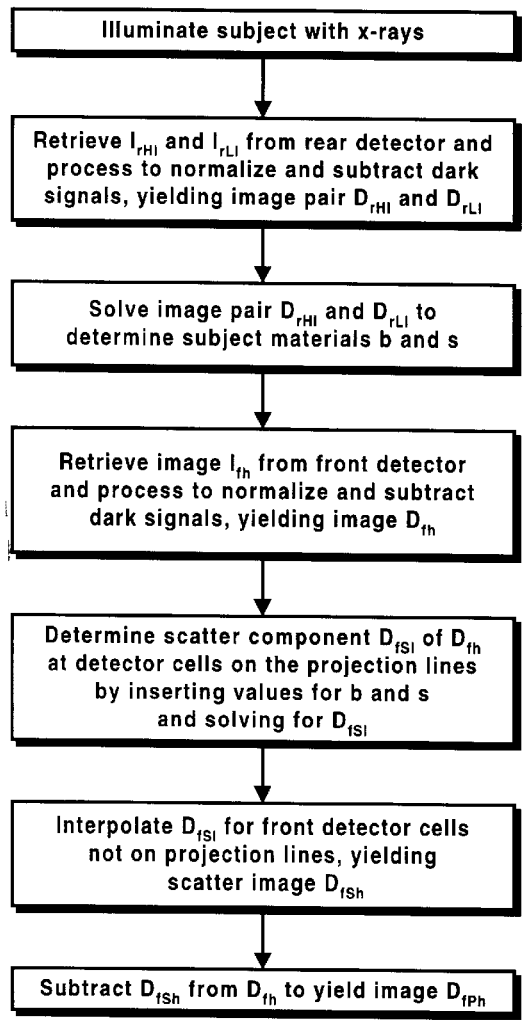
FIG. 4 is a flow diagram of the basic method to eliminate scatter using the hardware of FIG. 1.

The method for eliminating scatter, shown in the flow diagram of FIG. 4, consists of the following steps: (1) illuminating the subject with x-rays from the x-ray source 14; (2) acquiring a low-resolution image pair $I_{rHl}(i,j)$ and $I_{rLl}(i,j)$ from the rear detector assembly and processing it to normalize and to subtract dark signals, yielding a low-resolution image pair $D_{rHl}(i,j)$ and $D_{rLl}(i,j)$ that are functions of the subject materials, where "acquiring an image" is defined as transferring, via electronic control circuits, the electrical signals induced by the x-ray illumination on each detector cell from a detector array to computer memory; (3) solving the image pair $D_{rHl}(i,j)$ and $D_{rLl}(i,j)$ to determine the selected projection mass density of the subject materials b(i,j) and s(i,j); (4) acquiring a high-resolution image $I_{fh}(X,y)$ from the front detector and processing it to normalize and to subtract dark signals, yielding a high-resolution image $D_{fh}(X,Y)$, which is the sum of primary x-rays and scatter x-rays; (5) calculating the low-resolution primary image of the front detector $D_{fpl}(x(i),y(j))$ at the detector cells on the selected projection lines from the mass projection densities b(i,j) and s(i,j); (6) subtracting $D_{fpl}(x(i),y(j))$ from $D_{fh}(x(i),y(j))$ to calculate the low-resolution scatter component $D_{fSl}(x(i),y(j))$ of the image $D_{fh}(X(i),y(j))$ at the detector cells on selected projection lines; (7) interpolating $D_{fSl}(x(i),y(j))$ for those front detector cells not on the selected projection lines, yielding the high-resolution scatter image $D_{fSh}(X,y)$; and (8) subtracting the image $D_{fSh}(x,y)$ from $D_{fh}(x,y)$ to yield an image $D_{fph}(x,y)$, which is a full two-dimensional image of the subject at the front detector after scatter x-rays have been substantially eliminated.

The first step consists of illuminating the subject to produce a pair of primary images with high-energy x-rays and low-energy x-rays. There are two approaches to accomplishing this. The first approach is to use two sequential x-ray pulses of different energy levels. For this approach, only one detector array is necessary in the rear detector assembly 26 because the two energy levels are temporally separated. The second approach is to use a pulse or a continuous x-ray emission that spans a single spectrum of energies. For this approach, two detector arrays are needed in the rear detector assembly 26, where one detector detects the high-energy x-rays and the other detects the low-energy x-rays.

The second step consists of acquiring a pair of low-resolution images $I_{rHl}(i,j)$, $I_{rLl}(i,j)$ from the rear detector 26. The image pair $I_{rHl}(i,j)$, $I_{rLl}(i,j)$ is processed by computer software to normalized the data and to subtract dark signals. Both of these procedures must be used by any x-ray imaging technology and are well known in the art. Throughout this specification, all images acquired from the detectors 16, 26 are assumed to have been processed to normalized the data and to subtract dark signals following the image acquisition. The present invention only deals with the case where x-ray signal is much greater than the dark current signal. The resulting image pair $D_{rHl}$, $D_{rLl}$ constitutes a dual-energy x-ray primary image pair.

The third step consists of determining the subject material compositions b and s from the image data pair $D_{rHl}(i,j)$, $D_{rLl}(i,j)$. For each pair of dual-energy x-ray data $(D_{rH},D_{rL})$ at the point (i,j), a pair of material composition data (b,s) along the selected projection line can be determined from the data base provided by the data decomposition method, as explained below.

The fourth step consists of acquiring the high-resolution image $I_{fh}(x,y)$ from the front detector 16 and processing it to normalized the data and to subtract dark signals, yielding the high-resolution image $D_{fh}(X,Y)$.

The fifth step consists of producing the low-resolution component of the image $D_{fh}(x,y)$ at the front detector cells on the selected projections lines (x(i),y(j)). The low resolution component $D_{fl}(x(i),y(j))$ is a portion of the high-resolution image $D_{fh}(x,y)$ at the front detector and both contain primary and scatter x-rays. On the other hand, the primary component of the front detector image $D_{fpl}(x(i),y(j))$ can be calculated from the rear detector signals. By using the data base $D_H(b,s)$ and $D_L(b,s)$ provided by the data decomposition method for the front detector assembly 16, the signal pair $D_H$, $D_L$ for the front detector assembly is determined through the use of the subject material compositions b(i,j) and s(i,j) found in step 3. If the front detector assembly 16 has only one detector array, the corresponding signal is $D_{fpl}(b,s)$. Then the primary x-ray signal on the front detector $D_{fpl}(x(i),y(j))=D_{fpl}(b(i,j),s(i,j))$.

As explained above, the images from the rear detector assembly 26 are free of scatter. Thus, the calculated front detector primary image $D_{fpl}(x(i),y(j))$ is rigorous, accurate, and free of scatter. Then, through the sixth step, the scatter image from the front detector assembly 16 is further found from the equation $$D_{fsl}(x(i),(j))=D_{fl}(x(i),y(j)) -D_{fpl}(x(i),y(j)) \qquad (3)$$

which yields the scatter image at the front detector cells on the selected projection lines, or the low-resolution scatter image of the front detector.

The seventh step consists of interpolating the values for the low-resolution scatter image $D_{fsl}(x(i),y(j))$ to include those detector cells that are not on selected projection lines, yielding a high-resolution scatter image $D_{fsh}(x,y)$. The interpolation does not cause loss of accuracy because of the nature of the physical scattering process. The scatter 34 is essentially caused by Compton scattering, which has a substantially uniform angular distribution in the preferred x-ray energy range. Both empirical data and theoretical calculations show that scatter always has a substantially smooth distribution on a two-dimensional image plane. This means that the change in scatter intensity between adjacent cells is small and smooth. Thus, as long as there are a sufficiently large number of detector cell data points, the error incurred due to interpolation is negligible in comparison with other error sources, such as statistical fluctuations of x-ray photon numbers. Note an important difference between the scatter image and primary image. While the scatter image can be interpolated because of the nature of scatter, the primary image cannot be interpolated because the primary image changes with the subject 12 from detector cell to detector cell.

The final step consists of subtracting the high-resolution scatter image $D_{fsh}(x,y)$ from $D_{fh}(X,Y)$ using the following equation derived from equation 2, $$D_{fph}(x,y)=D_{fh}(x,y)-D_{fsh}(X,Y) \qquad (4)$$

Equation 4 yields an image $D_{fph}(x,y)$ corresponding to an image that would result if only primary x-rays 32 impinged on the front detector 16.

Because the data decomposition method of the present invention is rigorous and accurate and the mathematical calculations can be performed with good precision, as long as the experimental image data acquired from the detectors 16, 26 is highly accurate, the final result will be a highly accurate primary image of the subject 12.

First embodiment

Figure 5:
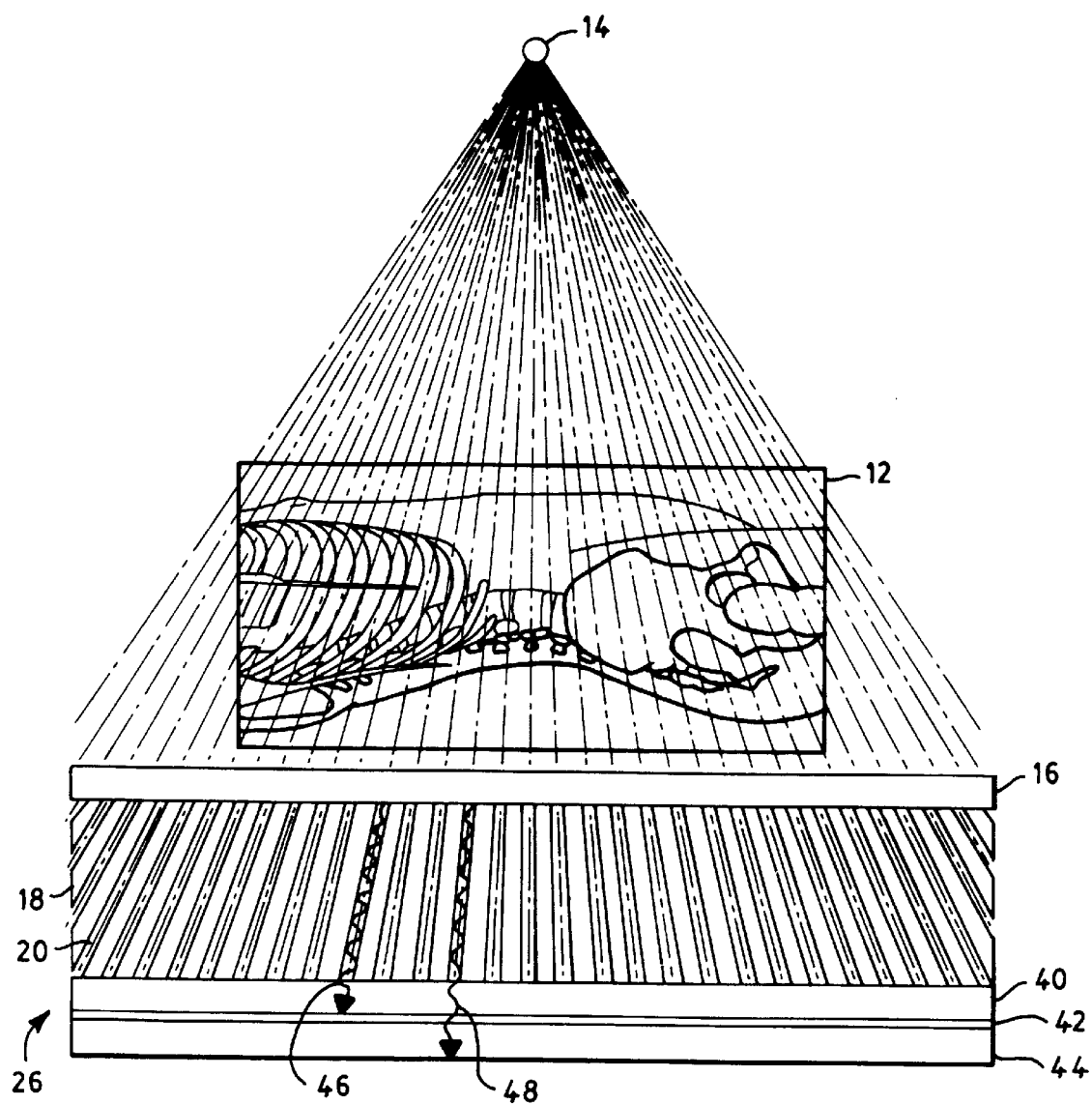
FIG. 5 is a diagram of the first embodiment of the present invention.

In the first embodiment of the apparatus, shown in FIG. 5, the rear detector assembly 26 is constructed as a dual-energy x-ray imaging detector assembly. It has a low-energy two-dimensional detector 40, an x-ray energy spectral filter 42, and a high-energy two-dimensional detector 44. The filter 42 operates in the conventional manner. It has a transmission function of $\exp(-\mu(E)\times d)$, where E is the energy of the x-rays, $\mu$ (E) is the mass absorption coefficient of the filter material, and d is the thickness of the filter 42. Because the absorption of x-rays is dependent upon the energy of the x-rays (the mass absorption coefficient is a function of E), the filter 42 absorbs more of the low-energy x-rays 46 than high-energy x-rays 48. Thus, the proportion of high-energy x-rays 48 to low-energy x-rays 46 after the filter 42 is larger than before the filter 42 and the average normalized x-ray energy after the filter 42 is larger than before the filter 42. The image detected by the low-energy detector 40 is denoted by $D_{rL}(i,j)$ and the image detected by the high-energy detector 44 is denoted by $D_{rH}(i,j)$. Preferably, the low-energy x-rays have an average energy of from 10 keV to 100 keV and high-energy x-rays have an average energy of from 30 keV to 500 keV, with the high-energy x-rays having a higher energy than the low-energy x-rays.

The purpose of measuring a pair of dual-energy primary images $D_{rH}(i,j)$ and $D_{rL}(i,j)$ of the rear detector assembly is to provide data for uniquely determining the corresponding primary low resolution image $D_{fpl}(x(i),y(j))$ at the front detector. Note an essential difference between the present invention and prior art. In an attempt to determine a frame of image data for one detector, the methods of the prior art invariably use only one frame of image data from another detector supplemented with certain calibration data, which establish the general quantitative relationship between the two detectors. One of the typical recent instances of such methods can be found, for example, in J. Y. Lo et al., *Scatter Compensation in Digital Chest Radiography Using the Posterior Beam Stop Technique*, 21 Medical Physics 437 (1994). In contrast to the methods of prior art, for the purpose of uniquely determining the primary image at the front detector, the present invention requires (1) the use of two frames of image data of another detector such as the rear detector, (2) where the data are from primary signals and free of scatter, and (3) the two frames of image data are a dual-energy image pair, with one for a high-energy image and the other for a low-energy image acquired at otherwise substantially identical conditions. It is explained below why all the methods of prior art invariably fail to eliminate scatter, and why only when these three conditions are fulfilled, the challenging task of eliminating scatter becomes possible. Note also the importance of blocking the scatter component at the selected locations on the rear detector assembly. If the primary x-rays are blocked, the rear detector assembly would receive only scatter x-rays, and there would be no way to uniquely determine the front detector images.

Figure 6:
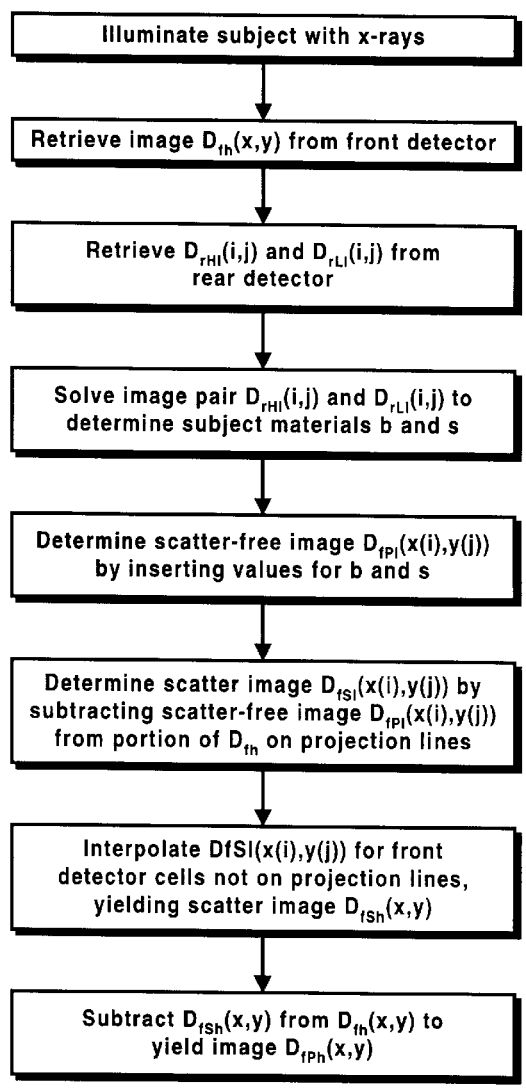
FIG. 6 is a flow diagram of the method of the first embodiment using the hardware of FIG. 5.

A flow diagram describing the method for determining a scatter-free image using the hardware of the first embodiment is shown in FIG. 6. The x-ray source 14 emits x-rays with a uniform angular distribution and with an energy spectrum of $\Phi_O(E)$. The x-rays passing through the subject 12 carry information on the thickness and material composition of the subject 12, expressed as projection mass density in units of grams/centimeters$^2$ (g/cm$^2$). The image induced by the x-rays incident on the front detector 16 is denoted as Dfh(x,y) and is $$D_{fh}(x,y) = \int [\Phi_0(E) \times \exp(-(\mu_b(E) \times b(x,y) + \mu_s(E) \times s(x,y))] \times S_f(E)dE + \int \Phi_S(E) \times S_f(E)dE \quad (5)$$

where $\mu_b(E)$ is the mass absorption coefficient of bone tissue and $\mu_s(E)$ is the mass absorption coefficient of soft tissue, with both $\mu_b(E)$ and $\mu_s(E)$ expressed in units of centimeter$^2$/gram (cm$^2$/g). Both of these values are known, having been determined experimentally and tabulated many years ago. The term $[(\Phi_O(E)\times\exp(-(\mu_b(E)\times b(x,y) +\mu_s(E)\times s(x,y))]$ is the energy spectrum of the primary x-rays incident on the front detector 16 after passing through the subject 12, where exp ( ) denotes the value e raised to the power specified in the parenthesis. $S_f(E)$ is the x-ray spectral sensitivity (the electrical signal amplitude from the detector as a function of the number of x-rays with energy E incident upon the detector) of the front detector 16. Note that Sf(E) includes not only the x-ray spectral sensitivity of the detector itself, but also the x-ray transmission factor that accounts for the absorption of x-rays between the subject 12 and the front detector 16. Such absorption is due, for example, to the front detector protective case material. The term $\int \Phi_s(E)\times S_f(E)dE$ represents the signal caused by scatter. The exact expression for the scatter is not known because the scattering process is too complicated to model mathematically. The coordinate (x,y) corresponds to a front detector cell.

The rear detector assembly 26 has two detectors 40, 44, so there are two low-resolution images $D_{rL}(i,j)$ and $D_{rH}(i,j)$, which are $$D_{rL}(i,j)=\int[\Phi_O(E)\times\exp(-(\mu_b(E)\times b(i,j)+\mu_s(E)\times s(i,j))]\times S_{rL}(E)dE \quad (6a)$$

and $$D_{rH}(i,j)=\int[\Phi_O(E)\times\exp(-(\mu_b(E)\times b(i,j)+\mu_s(E)\times S(i,j))]\times S_{rH}(E)dE \quad (6b)$$

Note that, as above, $S_{rL}(E)$ and $S_{rH}(E)$ include the x-ray transmission factors that account for the absorption of x-rays between the subject 12 and the respective rear detectors 40, 44. Such absorption for $S_{rH}(E)$ is due, for example, to the front detector assembly 16, the spectral filter 42, the rear detector protective case, and the rear low-energy detector.

Equations 6a and 6b constitute a simultaneous equation system, where the values for the signal pair $D_{rL}(i, i)$, $D_{rH}(i,j)$ are known quantities, being evaluated from the electrical signals of the rear detectors 40, 44. The energy dependent functions $\Phi_O(E)\times S_{rL}(E)$ and $\Phi_O(E)\times S_{rH}(E)$ are not directly known but can be determined in a calibration process. The data decomposition method described below provides a way to determine these quantities in advance of image operations. b(i,j) and s(i,j) are the unknown quantities for which equation pair 6a, 6b must be solved, as described below. Generally speaking, in mathematics, such a nonlinear simultaneous equation system is too complicated to be solvable because it may have an infinite number of solutions, may have multiple-value solutions, or may not have any solution. However, for the specific physical case of x-ray imaging, where the energy range is limited, preferably between 10 keV and 500 keV, it can be mathematically proved that a unique solution always exists for the nonlinear equation system 6a and 6b.

Accurate b(i,j) and s(i,j) are calculated by the data decomposition method of the present invention, as will be described below. Now that the values for b(i,j) and s(i,j) are known, the front low-resolution scatter-free image $D_{fPl}(x,y)$ can be obtained for those front detector cells (x(i),y(j)) that are on the selected projection lines. $D_{fPl}(x(i),y(j))$ is the signal induced by only primary x-rays at the detector cell (x(i),y(j)) on the front detector, and is $$D_{fPl}(x(i),y(j)) = \int [\Phi_0(E) \times \exp(-(\mu_b(E) \times b(i,j) + \mu_s(E) \times s(i,j))] \times S_f(E)dE \quad (7)$$

where (x(i),y(j)) is the coordinate of the front detector cell (x,y) lying on the same selected projection line as the rear detector cell (i,j) and the energy dependent function $\Phi_O(E) \times S_f(E)$is given in calibration, as will be described in the data decomposition section below.

Next, the low-resolution front scatter image $D_{fSl}(x(i),y(j))$ is determined by applying equation 3, $$D_{fSl}(x(i),(j))=D_{fl}(x(i),y(j))-D_{fPl}(x(i),y(j))$$

Because of the physical nature of scatter, as described above, the low-resolution scatter image $D_{fSl}(x(i),y(j))$ can be extended to the entire (x,y) plane through interpolation without losing accuracy, yielding the high-resolution scatter image $D_{fSh}(x,y)$. The high-resolution scatter image $D_{fSh}(x,y)$ is subtracted from the experimentally measured image $D_{fh}(x,y)$, yielding the high-resolution scatter-free signal $D_{fPh}(x, y)$.

It is now clear why it is crucial to acquire a pair of dual-energy x-ray images $D_{rL}(i,j)$, $D_{rH}(i,j)$ to determine the scatter. The primary signals at the front detector $D_{fPl}(x(i),y(j))$ can be uniquely determined only when the material composition image pair b(i,j) and s(i,j) is known (see equation 7). The two material composition images b(i,j) and s(i,j) can only be uniquely determined from a pair of dual-energy images $D_{rL}(i,j)$, $D_{rH}(i,j)$. To put it another way, because the x-rays have a broad continuous spectrum, no constant ratio exists between the signals measured by the front detector and the signals measured by the rear detector. If only one image at the rear detector is used, it would always be found that the signal ratio between the front detector and the rear detector is dependent on the energy spectrum [$\Phi_O(E) \times \exp(-(\mu_b(E) \times b(i,j) + \mu_s(E) \times S(i,j))$], or dependent on the image subject, which changes drastically from one case to another case and from one projection line to another. Consequently, the primary image on the front detector could not be determined.

Therefore, the fundamental physical law of dual-energy x-ray imaging dictates that to uniquely determine the primary image at the front detector, a dual-energy primary image data pair must be used. The prior art fails to recognize this, invariably giving a highly undesirable result: the scatter image data obtained for conducting scatter correction is dependent on the image subject present in the measurements.

It is also noted that, as a supplement to this general rule, there are two special cases where the relationship between the signals on the image plane (i,j) and the image plane (x(i),y(j)) can be degenerated or simplified to be proportional to each other and independent of the image subject. Thus, for correcting scatter, it is not necessary to use the dual-energy method for these two special cases.

The first special case occurs when the range of the x-ray energy spectral distribution is sufficiently narrow so that the x-rays can be approximated as having only a single energy or a well-defined average energy Eo. The signals on the front detector become $$D_{fP1}(x(i),y(j)) = \Phi_0(E_o) \times \qquad (8a)$$

$$\exp(-(\mu_b(E_o) \times b(x(i),y(j)) + \mu_s(E_o) \times s(i,j)) \times S_f(E_o)$$

and the signals on the rear detector become $$D_{r1}(i,j) = \Phi_O(E_O) \times \exp(-(\mu_b(E_O) \times b(i,j) + \mu_s(E_O) \times s(i,j))) \times S_r(E_O) \qquad (8b)$$

yielding.

$$\frac{D_{fP1}(x(i),y(j))}{D_{r1}(i,j)} = \frac{S_f(E_0)}{S_r(E_0)} = C_0(i,j) \qquad (9)$$

The constant $C_O(i,j)$ is independent of image subject and can be predetermined before using the system for imaging operations. Using the constant $C_O(i,j)$, the primary low-resolution image of the front detector $D_{fP1}(x(i),y(j))$ is directly calculated from the primary low-resolution image of the rear detector $D_{r1}(i,j)$.

Figure 7A:
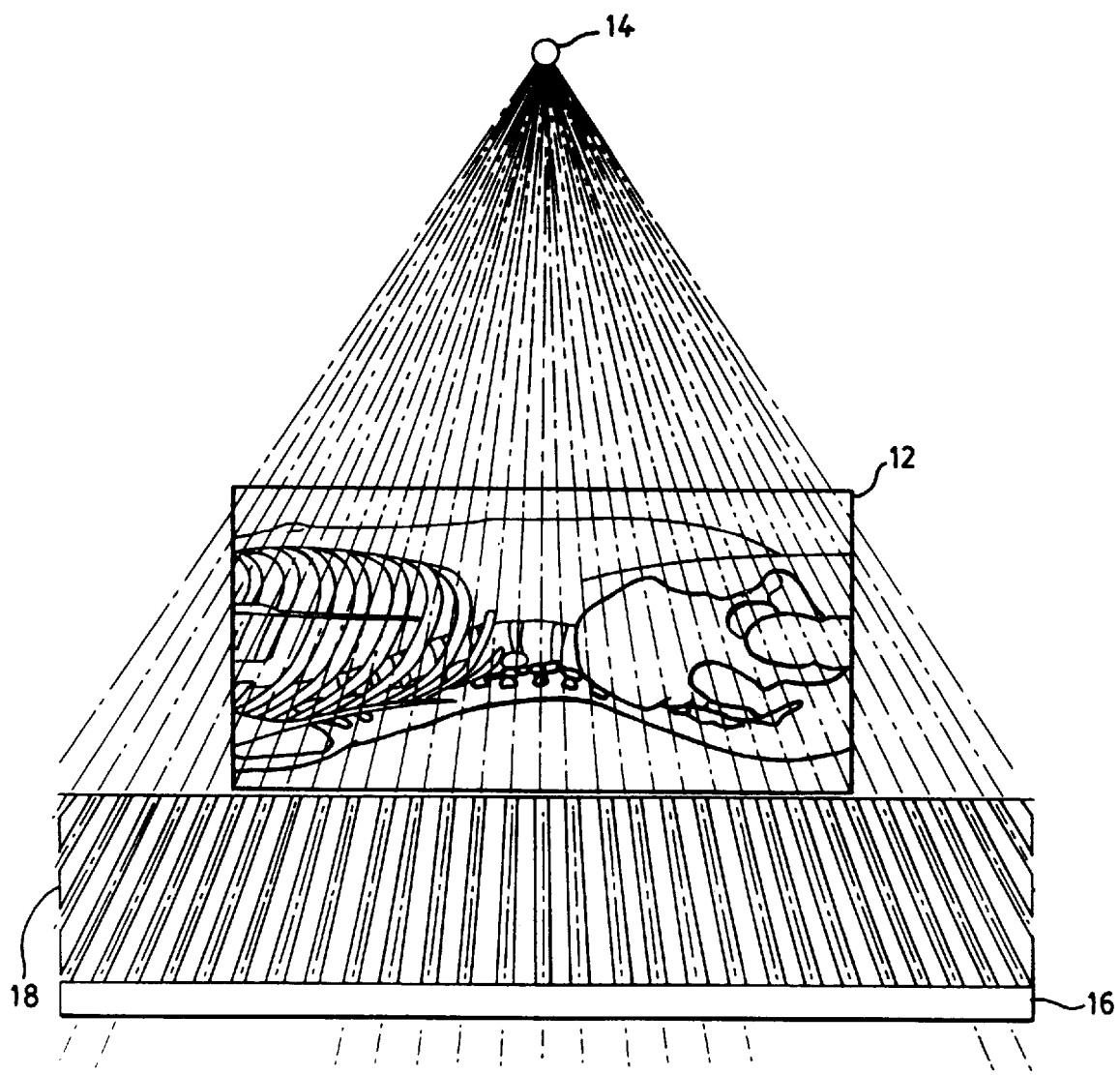
FIGS. 7a and 7b are diagrams of a special case of the first embodiment of the present invention.
Figure 7B:
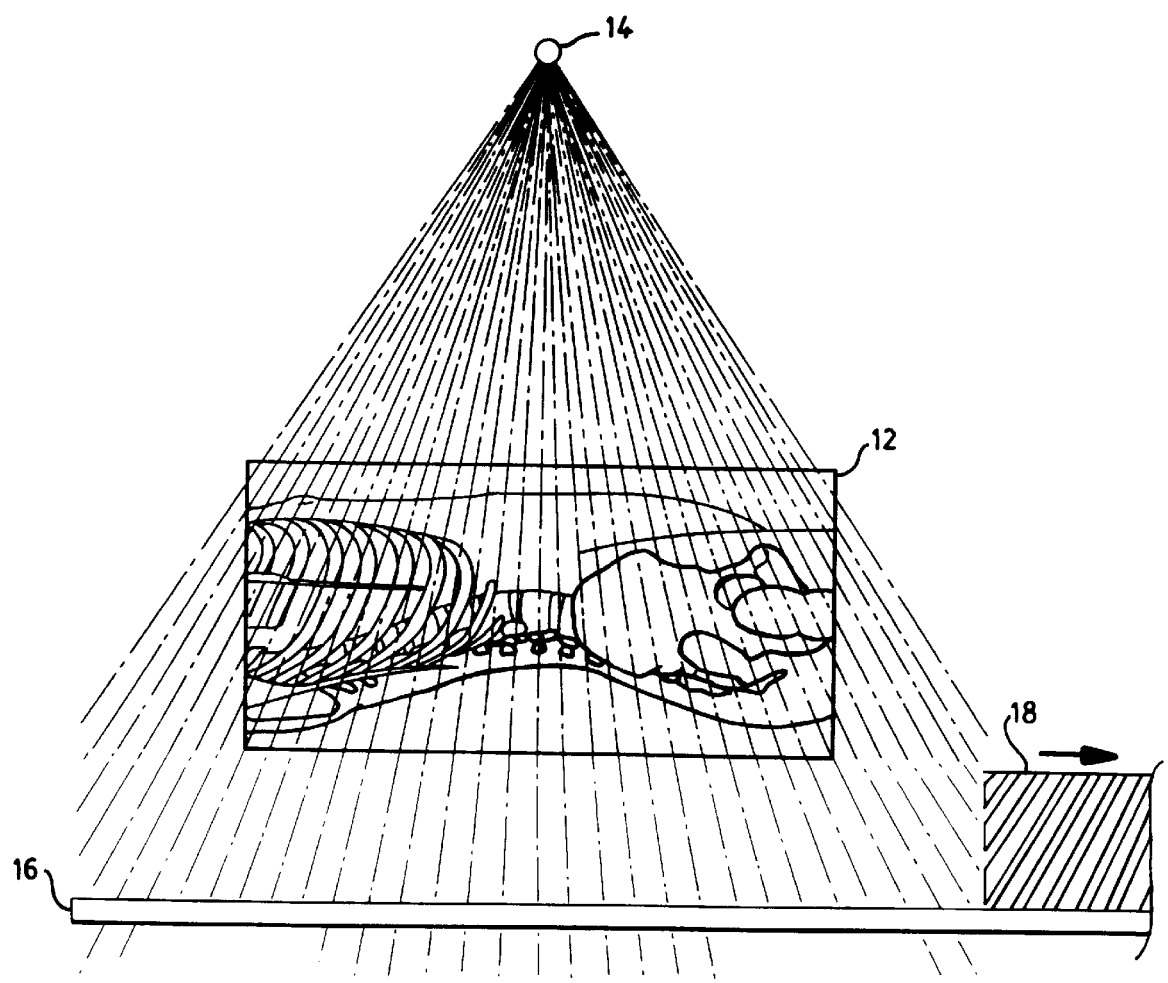

The second special case is shown in FIGS. 7a and 7b, where only one detector is used for acquiring both the high resolution image $D_{fh}(x,y)$ and the low resolution image $D_{rl}(i,j)$. A mechanical device moves the beam selector to and away from the detector's front surface. When the beam selector is present, as in FIG. 7a, blocking the scatter from reaching the detector, a low resolution image $D_{rl}(i,j)$ is acquired. When the beam selector is absent, as in FIG. 7b, allowing all x-rays to reach the detector, a high resolution image $D_{fh}(x,y)$ is acquired, a portion of which is $D_{fh}(x(i),y(j))$. Here the subscript f denotes that the beam selector 18 is in its transmissive position not in front of the detector 16 and the subscript r denotes that the beam selector 18 is in its blocking position in front of the detector 16. In this special case, when the rest conditions are maintained substantially identical, $$D_{rl}(i,j) = \int [\Phi_O(E) \times \exp(-(\mu_b(E) \times b(i,j) + \mu_s(E) \times s(i,j))] \times S_r(E) dE \qquad (10a)$$

and $$D_{fP1}(x(i),y(j)) = \int [\Phi_O(E) \times \exp(-(\mu_b(E) \times \qquad (10b)$$

$$b(i,j) + \mu_s(E) \times s(i,j))] \times S_f(E) dE$$

If, and only if, the x-ray beam transmission through the holes is 100%, an energy-independent constant exists: $S_f(E) = C_g(i,j) \times S_r(E)$], where $C_g(i,j)$ is independent of the image subject 12 and is predetermined when the image subject 12 is absent.

$$D_{fP1}(x(i),y(j)) = C_g(i,j) \times D_{r1}(i,j) \qquad (11)$$

Figure 8:
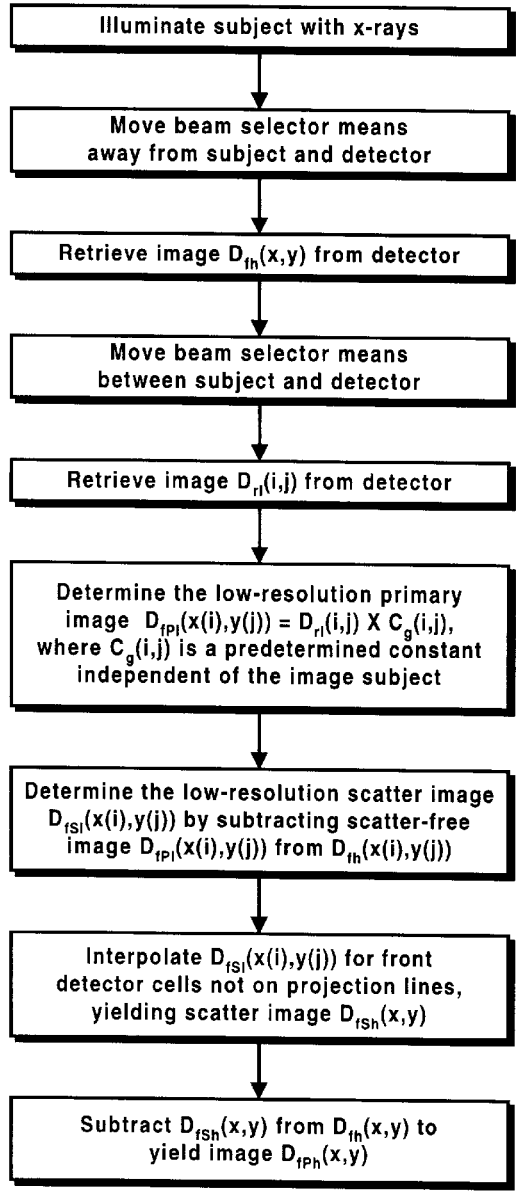
FIG. 8 is a flow diagram of the method of the special case using the hardware of FIGS. 7a and 7b.

FIG. 8 shows the data processing procedures for the second special case.

Note that if the x-ray beam transmission through the holes is less than 100%, due to the change of the x-ray energy spectrum, generally no such proportional relationship exists. Then, to determine the primary image $D_{fP1}(x(i),y(j))$ at the front detector from the rear detector data, even if the front and rear detector are the same detector, dual-energy methods must still be used.

Second embodiment

Figure 9:
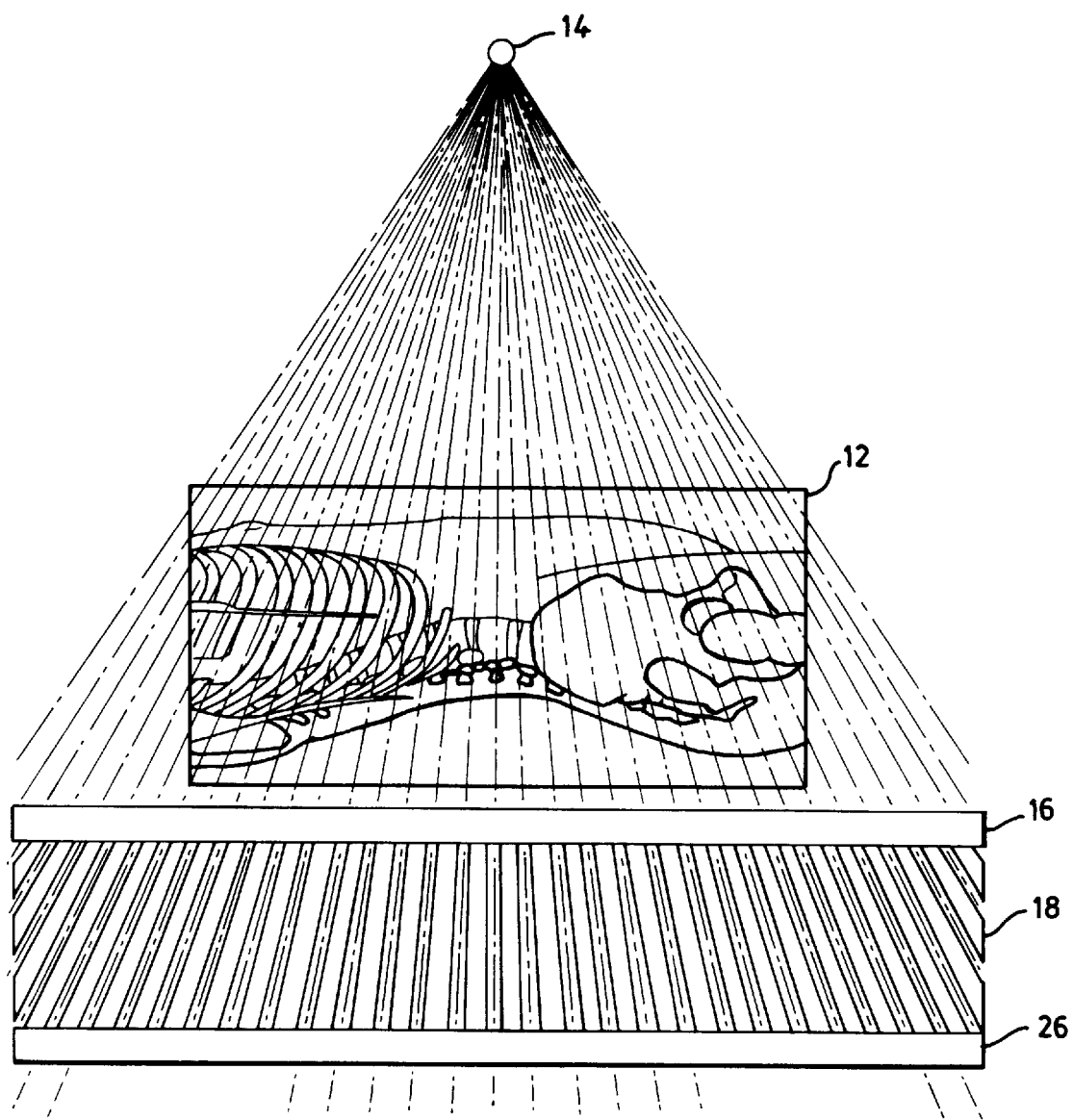
FIG. 9 is a diagram of the second embodiment of the present invention.

In this embodiment, shown in FIG. 9, the front detector assembly 16 and the rear detector assembly 26 each have only one detector. The x-ray source 14 emits two consecutive pulses, a low-energy pulse followed by a high-energy pulse. In an alternate configuration, the high-energy pulse is emitted first. Preferably, in both configurations, the low-energy pulse has an average x-ray energy from approximately keV to approximately 100 keV and the high-energy pulse has an average x-ray energy from approximately 30 keV to approximately 500 keV, with the high-energy pulse always higher in energy than the low-energy pulse.

Figure 10:
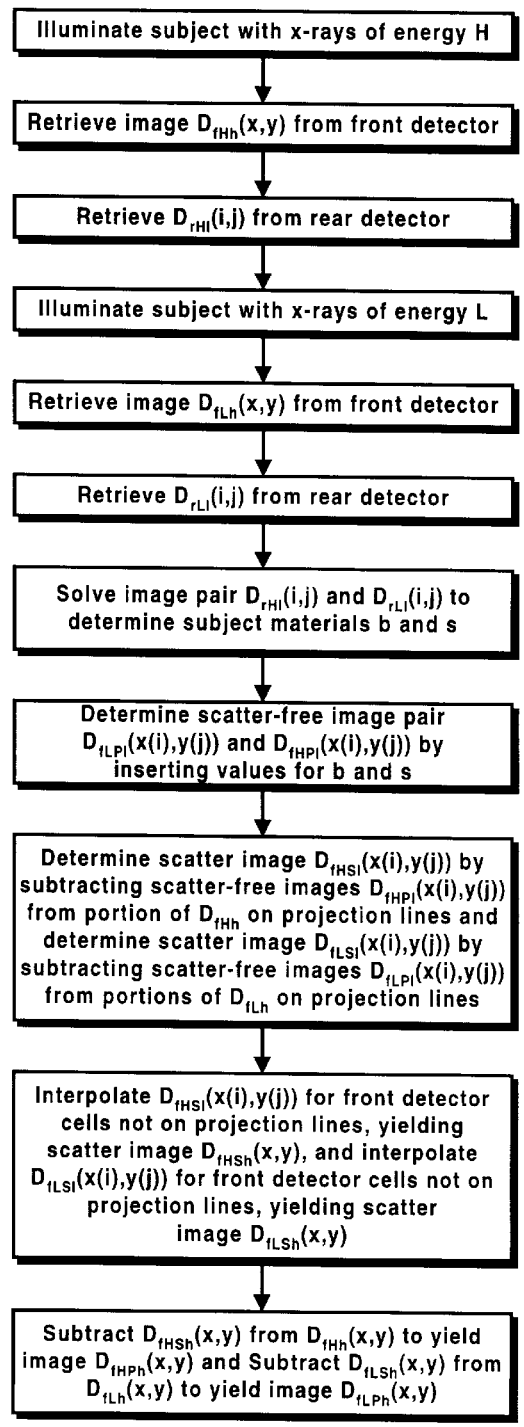
FIG. 10 is a flow diagram of the method of the second embodiment using the hardware of FIG. 9.

As described with respect to the first embodiment above, the low-resolution scatter-free image pair $D_{rLf}(i,j)$, $D_{rHf}(i, i)$ from the rear detector is used to first determine the low-resolution primary image pair on the front detector 16 and then to determine the low resolution scatter image pair on the front detector 16. In this embodiment, a pair of low-resolution scatter images $D_{fHSl}(x(i),x(j))$, $D_{fLSl}(x(i),x(j))$ is obtained for the front detector 16 operated at high energy and at low energy, respectively. After interpolation of the resulting scatter image pair to a high-resolution image pair $D_{fHSh}(x,y)$, $D_{fLSh}(x,y)$ to cover all (x,y) cells and subtracting the high-resolution scatter image pair from the directly measured image pair $D_{fLh}(x,y)$ and $D_{fHh}(X,y)$, a pair of high-resolution scatter-free images $D_{fLPh}(x,y)$, $D_{fHPh}(x,y)$ is obtained. The method is detailed as follows:

As shown in FIG. 10, the high-resolution image $D_{fHh}(x,y)$ is acquired from the front detector 16 and the lowresolution image $D_{rHl}(i, i)$ is acquired from the rear detector 26 following the high-energy x-ray pulse. The highresolution image $D_{fLh}(x,y)$ is acquired from the front detector 16 and the low-resolution image $D_{rLl}(i,j)$ is acquired from the rear detector 26 following the low-energy x-ray pulse. From these two consecutive operations of data acquisition, two pairs of images are obtained. The first pair includes the high-resolution images from the front detector 16 and are $$D_{fHh}(x,y) = \int [\Phi_{OH}(E) \times \exp(-(\mu_b(E) \times b(x,y) + \qquad (12a)$$

$$\mu_s(E) \times s(x,y))] \times S_f(E) dE + \int \Phi_{fS}(E,x,y) \times S_f(E) dE$$

and $$d_{fLh}(x,y) = \int [\Phi_{OL}(E) \times \exp(-(\mu_b(E) \times b(x,y) + \qquad (12b)$$

-continued $$\mu_s(E) \times s(x,y))] \times S_f(E)dE + \int \Phi_{fS}(E,x,y) \times S_f(E)dE$$

and the second pair includes the low-resolution images from the rear detector 26 and are $$D_{rHl}(i,j) = \int [\Phi_{OH}(E) \times \exp(-(\mu_b(E) \times b(i,j) + \mu_S(E) \times s(i,j))] \times S_r(E) dE \quad (13a)$$

and $$D_{rLl}(i,j) = \int [\Phi_{OL}(E) \times \exp(-(\mu_b(E) \times b(i,j) + \mu_S(E) \times s(i,j))] \times S_r(E) dE \quad (13b)$$

In the equation pair 13a, 13b, the acquired lowresolution image data are free of scatter radiation. By using the dual-energy data decomposition methods described below, the simultaneous equation pair 13a, 13b is solved to find the solutions for the image pair of material composition $b(i,j)$ and $s(i,j)$.

As described above with reference to the first embodiment, because each rear detector cell position in the $(i,j)$ plane corresponds to a known front detector cell position $(x(i),y(j))$ in the $(x,y)$ plane and because the rear detector cell $(i,j)$ and front detector cell $(x(i),y(j))$ lie on the same selected projection line, the low-resolution front detector primary image pair $D_{fHPl}(x(i),y(j))$, $D_{fLPl}(x(i),y(j))$ can be determined from the rear detector primary image pair $D_{rHl}(i,j)$, $D_{rLl}(i,j)$. The front detector scatter image pair $D_{fHSl}(x(i),y(j))$, $D_{fLSl}(x(i),y(j))$ are found by the equations $$D_{fHSl}(X(i),y(j)) = D_{fHl}(x(i),y(j)) - D_{fHPl}(x(i),y(j)) \quad (14a)$$

and $$D_{fLSl}(X(i),y(j)) = D_{fLl}(x(i),y(j)) - D_{fLPl}(x(i),y(j)) \quad (14b)$$

As above, the low-resolution scatter images can be extended to all front detector cells not on the selected projection lines through interpolation without loss of accuracy to yield the high-resolution scatter image pair $D_{fHSh}(X,Y)$, $D_{fLSh}(X,y)$. The high-resolution scatter-free images on the front detector assembly are denoted as $D_{fHPh}(x,y)$ and $D_{fLPh}(x,y)$ and are $$D_{fHPh}(x,y) = D_{fHh}(x,y) - D_{fHSh}(X,Y) \quad (15a)$$

and $$D_{fLph}(x,y) = D_{fLh}(x,y) - D_{fLSh}(x,Y) \quad (15b)$$

The image pair $D_{fHph}(x,y)$, $D_{fLph}(x,y)$ is a pair of dual-energy x-ray images without scatter. This image pair in turn relates to the material composition of the subject by the equations $$D_{fHPh}(X,Y) = \int [\Phi_{OH}(E) \times \exp(-(\mu_b(E) \times b(x,y) + \mu_S(E) \times s(x,y))] \times S_f(E) dE \quad (16a)$$

and $$D_{fLPh}(x,y) = \int [\Phi_{OL}(E) \times \exp(-(\mu_b(E) \times b(x,y) + \mu_S(E) \times s(x,y))] \times S_f(E) dE \quad (16b)$$

Thus, in addition to providing one scatter-free image, this embodiment provides a pair of scatter-free dual-energy images in the equation pair 16a, 16b. This equation pair is the fundamental dual-energy x-ray imaging equation system with the unprecedented feature that scatter radiation has been essentially removed from the two-dimensional detector. In the equation pair 16a, 16b, the values of $D_{fLPh}(x,y)$ and $D_{fHPh}(x,y)$ are known from the above described calculations conducted on the image pair $D_{fHh}(x,y)$ $D_{fLh}(x,y)$ directly measured from the front detectors 16, and on the image pair $D_{rLl}(i,j)$, $D_{rHl}(i,j)$ directly measured from the rear detector 26. The unknown values are the two material composition images $b(x,y)$ and $s(x,y)$.

The dual-energy x-ray data decomposition method can be further applied to the equation pair 16a, 16b. As a result, by using the quantitative relationships $b=b(D_H,D_L)$ and $s=s(D_H,D_L)$ provided by the data decomposition method, a pair 15 of high-resolution images $b(x,y)$ and $s(x,y)$ are readily obtained point by point for all front detector cells $(x,y)$. The solution of the two-component material composition images $b(x,y)$ and $s(x,y)$ has a spatial resolution as high as the front detector 16 can provide.

An alternate to the second embodiment substitutes an x-ray source having a switching high-voltage power supply. The switching high-voltage x-ray source generates x-rays continuously, alternating between high-energy x-rays and low-energy x-rays. The switching high-voltage x-ray source 25 can be treated as a repetitive double-pulse x-ray source.

Another alternate to the second embodiment inserts an x-ray energy filter between the x-ray source and the subject at the moment the x-ray source switches to generate the high-energy x-rays. The synchronization between the insertion of the filter and the switching high-voltage or double-pulse is preferably implemented by using a motor drive. The filter absorbs more of the low-energy x-rays, resulting in an increase in the energy difference between the low-energy x-rays and the high-energy x-rays.

From a technology point of view, the first embodiment and the second embodiment use essentially the same elements and essentially the same methods. However, from an application point of view, dual-energy x-ray imaging using two-dimensional detectors without scatter is an independent and very important area. The goal of dual-energy x-ray imaging is to find two material composition images of the subject at the spatial resolution as high as the two-dimensional detectors can provide. This invention not only provides a method and apparatus for removing scattering from two-dimensional detectors, but at the same time also provides a method and apparatus for scatter-free dual-energy x-ray imaging using two-dimensional detectors.

The interrelationship between the method for removing scatter radiation in two-dimensional detectors and the method for dual-energy x-ray imaging using two-dimensional detectors can be summarized as follows:

1. The method for removing scatter radiation from two-dimensional detectors utilizes and hinges on the method of dual-energy x-ray imaging free of scatter. Without dual-energy x-ray imaging, the scatter radiation cannot be accurately removed.

2. The method for dual-energy x-ray imaging using two-dimensional detectors utilizes and hinges on the method of removing scatter radiation. Without substantially removing scatter from two-dimensional detectors, the accuracy of dual-energy x-ray imaging would be so degraded as to be meaningless.

This invention solves both problems in a unified system. The methods of the prior art fail to solve either of the two problems. The most important reason may be attributed to the failure of prior art methods to recognize the interdependency of the removal of scatter and the use of dual-energy imaging.

Third Embodiment

Figure 11:
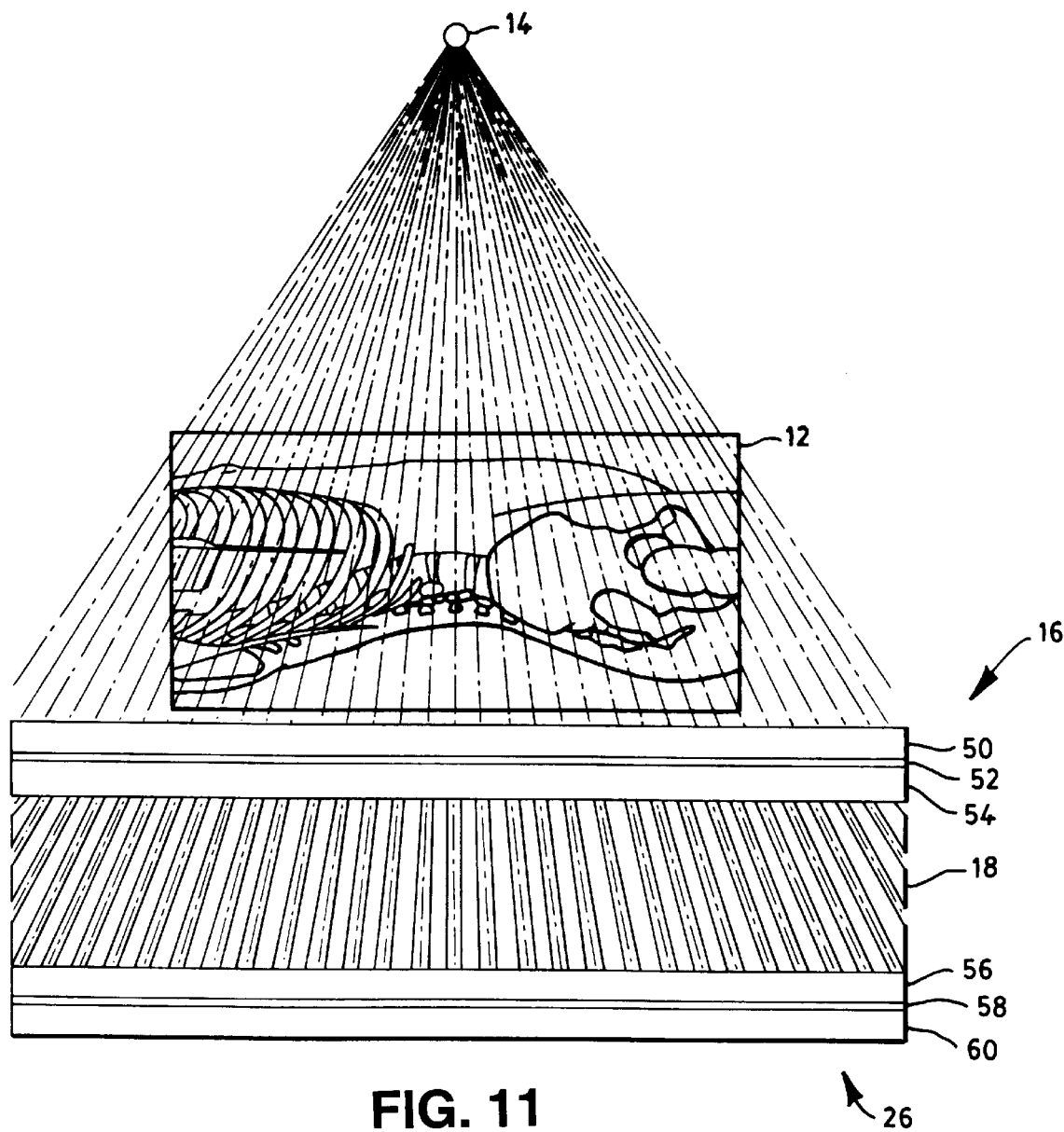
FIG. 11 is a diagram of the third embodiment of the present invention.

The third embodiment, shown in FIG. 11, is also a method for scatter-free dual-energy x-ray imaging using a pair of two-dimensional detector assemblies. The x-ray source 14 is a constant potential x-ray source that emits steady state x-rays, single pulse x-rays, or repetitive pulse x-rays with the same energy spectrum. The front detector assembly 16 has a low-energy two-dimensional detector 50, an x-ray energy spectral filter 52, and a high-energy two-dimensional detector 54. The rear detector assembly 26 also has a low-energy two-dimensional detector 56, an x-ray energy spectral filter 58, and a high-energy two-dimensional detector 60. The filters 52, 58 operate in the conventional manner as described above with reference to the first embodiment. The front high-energy detector 54 is sensitive to higher x-ray energies than the front low-energy detector 50 and the rear high-energy detector 60 is sensitive to higher x-ray energies than the rear low-energy detector 56. But, in addition, the rear low-energy detector 56 is sensitive to higher x-ray energies than the front high-energy detector 54. This is due to the fact that, by the time the x-rays reach the rear detector 26, they have already passed through the both front detectors 50, 54 and the front spectral filter 52, causing the lower-energy x-rays to have been filtered out.

Figure 12:
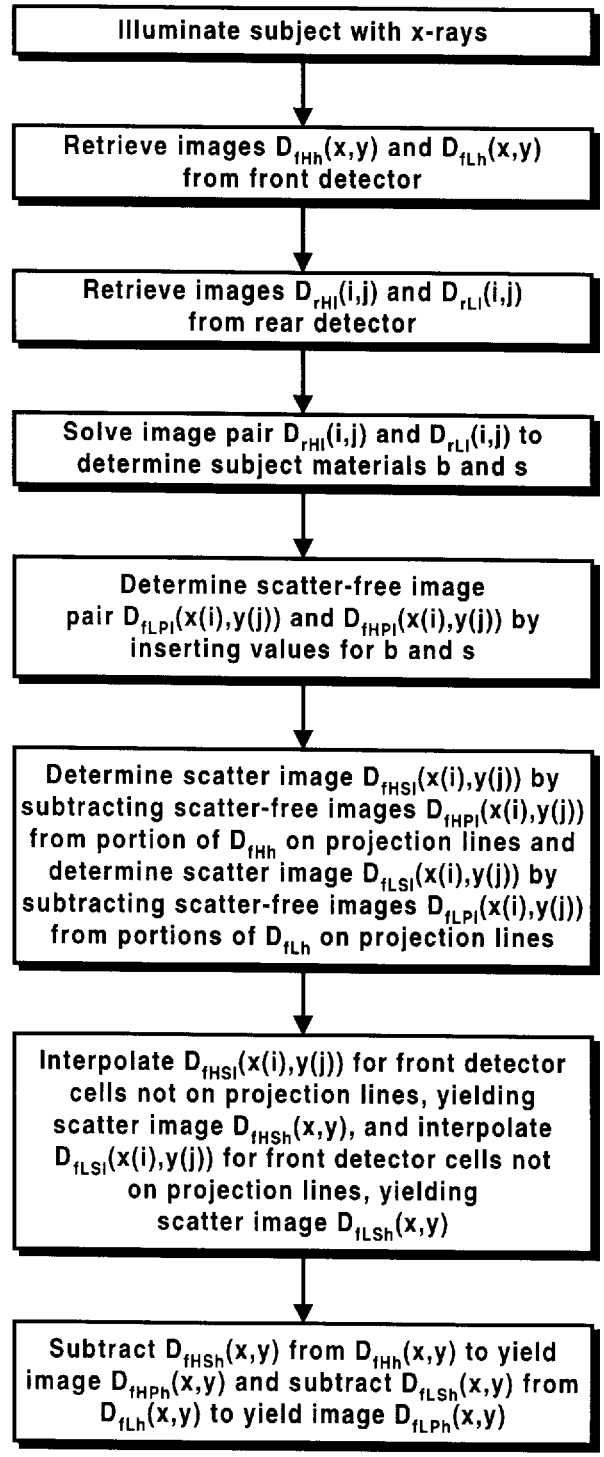
FIG. 12 is a flow diagram of the method of the third embodiment using the hardware of FIG. 11.

This embodiment requires only single-pulse, constant-energy x-rays, as in the first embodiment, rather than the dual-energy x-ray source of the second embodiment. As shown in FIG. 12, following a single-pulse x-ray, two pairs of dual-energy x-ray images are acquired. The first pair includes the high-resolution images $D_{fLh}(x,y)$ from the low-energy front detector 50 and $D_{fHh}(x,y)$ from the high-energy front detector 54, and are $$D_{fHh}(x,y) = \int [\Phi_0(E) \times \exp(-(\mu_b(E) \times b(x,y) + \quad (17a)$$
$$\mu_s(E) \times s(x,y))] \times S_{fH}(E)dE + \int {}_{fS}(E,x,y) \times S_{fH}(E)dE$$

and $$D_{fLh}(x,y) = \int [\Phi_0(E) \times \exp(-(\mu_b(E) \times b(x,y) + \quad (17b)$$
$$\mu_s(E) \times s(x,y))] \times S_{fL}(E)dE + \int \Phi_{fS}(E,x,y) \times S_{fL}(E)dE$$

and the second pair includes the low-resolution images $D_{rLl}(i,j)$ from the low-energy rear detector 56 and $D_{rHl}(i,j)$ from the high-energy rear detector 60 and are $$D_{rHl}(i,j) = \int [\Phi_0(E) \times \exp(-(\mu_b(E) \times b(i,j) + \quad (18a)$$
$$\mu_s(E) \times s(i,j))] \times S_{rH}(E)dE$$

and $$D_{rLl}(i,j) = \int [\Phi_0(E) \times \exp(-(\mu_b(E) \times b(i,j) + \quad (18b)$$
$$\mu_s(E) \times s(i,j))] \times S_{rL}(E)dE$$

Note that, because a single x-ray source is used, the x-ray energy spectrum $\Phi_O(E)$ is the same for all of the images. Note also that $S_{fH}(E)$, $S_{fL}(E)$, $S_{rH}(E)$, and $S_{rL}(E)$ include not only the energy spectral sensitivity of the corresponding detector but also include all transmission factors that account for x-ray absorption between the subject and the respective detector.

As described above with relation to the second embodiment, the simultaneous equation pair 18a, 18b does not contain scatter and holds true for each point in the rear image plane (i,j). Thus, equation pair 18a, 18b can be solved to yield a pair of material composition images b(i,j), s(i,j) for each cell in the (i,j) plane. This image pair is used to first determine the low-resolution primary image pair $D_{fHPl}(x(i),y(j))$, $D_{fLPl}(x(i),y(j))$ and then to determine scatter image pair $D_{fHSl}(x(i),y(j))$, $D_{fLSl}(x(i) y(j))$ in the same way as for the equation pair 14a, 14b. Scatter image pair $D_{fHSl}(x(i),y(j))$, $D_{fLSl}(x(i),y(j))$ is used to further determine the high-resolution scatter image pair $D_{fHSh}(x,y)$, $D_{fLSh}(x,y)$, as described above in the second embodiment. By subtracting the calculated high-resolution scatter image pair $D_{fHSh}(x,y)$, $D_{fLSh}(x,y)$ from the front detector 16 high-resolution image pair $D_{fHh}(x,y)$, $D_{fLh}(x,y)$, the high spatial resolution image pair free of scatter $D_{fHPh}(x,y)$ and $D_{fLPh}(x,y)$ is numerically obtained. At this point, the fundamental dual-energy equations in high spatial resolution can be used for obtaining the material composition image pair b(x,y) and s(x,y), $$D_{fLPh}(x,y) = \int [\Phi_o(E) \times \exp(-(\mu_b(E) \times b(x,y) + \quad (19b)$$
$$\mu_s(E) \times s(x,y))] \times S_{fL}(E)dE$$

and $$D_{fHPh}(x,y) = \int [\Phi_o(E) \times \exp(-(\mu_b(E) \times b(x,y) + \quad (19a)$$
$$\mu_s(E) \times s(x,y))] \times S_{fH}(E)dE$$

Using the inversion method described below, a pair of high-accuracy, high-resolution material composition images b(x,y) and s(x,y) are obtained.

Data Decomposition Method

Figure 3:
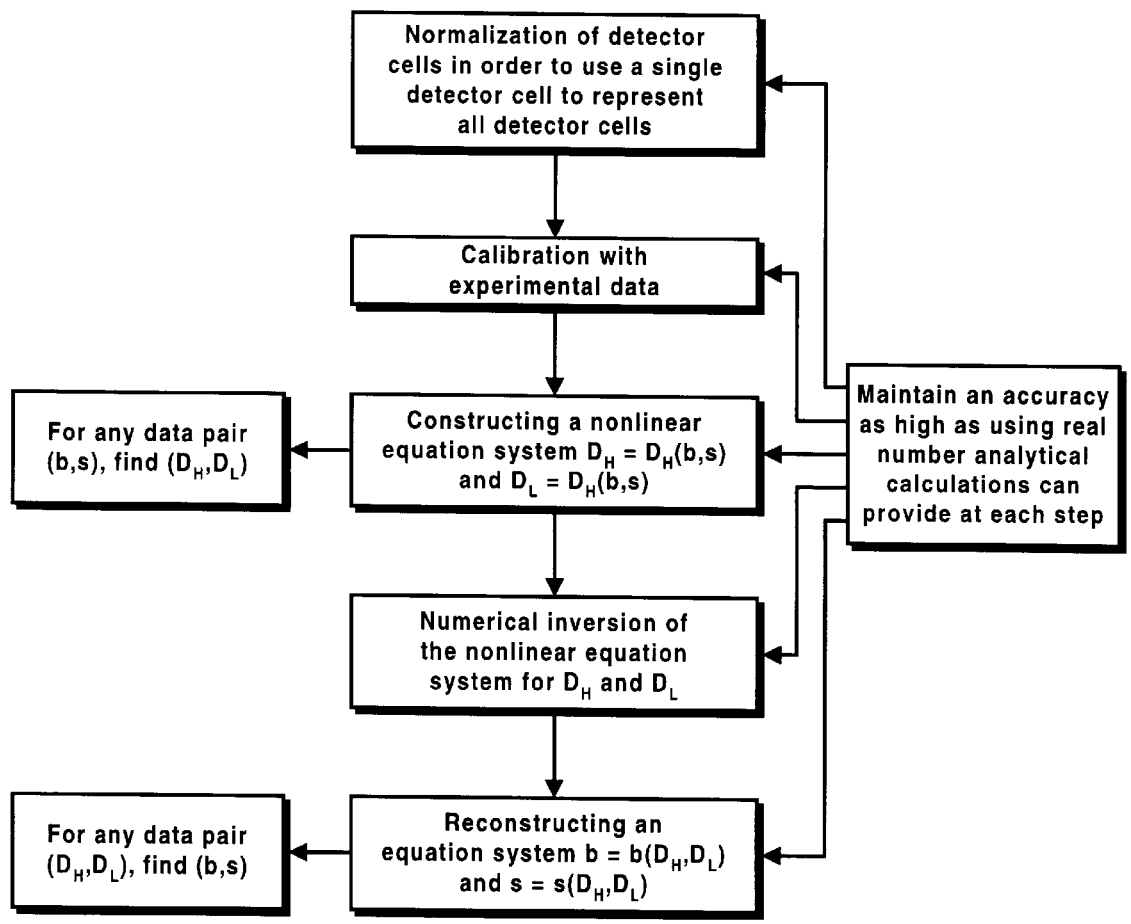
FIG. 3 is a flow diagram of the basic dual-energy data decomposition method using the hardware of FIG. 1.

The following is a step-by-step description of the data decomposition method summarized above and shown in FIG. 3.

The first step is to construct the two simultaneous numerical surface equations $D_L = D_L(b,s)$ and $D_H = D_H(b,s)$ in three-dimensional space. A preferred method to do this is to determine the detection system energy-dependent functions and use these functions to calculate the numerical arrays for $D_L$ and $D_H$.

Note that there is a difference between equation pair 19a, 19b and equation pair 16a, 16b. If a unified notation is used, the two pairs have the same form. The system energy-dependent function of a detector, denoted sps(E), is defined as $$sps(E) = \Phi_o(E) \times S(E) \quad (20)$$

where $\Phi_o(E)$ is the x-ray energy spectrum emitted from the x-ray source 14 and S(E) is the energy response function of the detector. In the second embodiment, the equation pair 16a, 16b becomes $$sps_H(E) = \Phi_{OH}(E) \times S_f(E) \quad (21a)$$

$$sps_L(E) = \Phi_{OL}(E) \times S_f(E) \quad (21b)$$

and in the third embodiment, the equation pair 19a, 19b becomes $$sps_H(E) = \Phi_O(E) \times S_{fH}(E) \quad (22a)$$

$$sps_L(E) = \Phi_O(E) \times S_{fL}(E) \quad (22b)$$

The function sps(E) contains the complete energy-dependent features of the dual-energy imaging system. The advantage of determining sps(E) is that all subsequent data processing methods are made independent of the subject 12.

A preferred method for determining the energy-dependent function sps(E) of the imaging system is to use the well-established absorption method. An example of application of the absorption method is found in Benjamin R. Archer & Louis K. Wagner, *A Laplace Transform Pair Model for Spectral Reconstruction*, 9 Medical Physics 844 (Nov/Dec 1982). An absorption curve is measured by using a collimated narrow primary x-ray beam. An absorption plate composed of a known material, such as aluminum, Lucite®, or copper, is placed between the x-ray source and the detector. The electrical signal from a single detector cell D(t) as a function of the absorption plate thickness t is experimentally determined and is related to sps(E) through the equation $$D(t) = \int sps(E) \times exp(-\mu(E) \times t) dE \quad (23)$$

Since the mass absorption coefficient $\mu(E)$ of the absorption plate material is known, the function sps(E) can be determined to the accuracy required by the dual-energy x-ray imaging. This method is especially convenient for the internal conversion type of two-dimensional x-ray detectors. In these detectors, the detection efficiency and detector energy response function can be expressed in a simple analytical expression with few unknown parameters to be solved. The energy response function for internal conversion type of detectors is written as:

$$S(E) = S_0(E) \times S_1(E) \quad (24a)$$

or $$S(E) = \{[1-exp(-\mu_0(E) \times d)] \times \alpha E\} \times exp(-\mu_1(E) \times d_1 - \mu_2(E) \times d_2) \quad (24b)$$

where $S_0(E) = [1-exp(-\mu_0(E) \times d)] \times \alpha E$ is the electrical signal amplitude induced by x-ray photons with energy E, $\mu_0(E)$ is the mass absorption coefficient of the detector's conversion layer, d is the thickness of the conversion layer of the detector cell, and where $S_1(E) = exp(-\mu_1(E) \times d_1 - \mu_2(E) \times d_2)$ is the x-ray transmission after leaving the image subject to the detector surface, $\mu_1(E)$ and $\mu_2(E)$ are the absorption coefficients of two given materials, and $d_1$ and $d_2$ are the thickness values of these materials.

When the x-ray energy spectrum $\Phi_0(E)$ is separately measured, these unknown parameters $\alpha$, d, $d_1$, and $d_2$ are determined by using standard least square parameter-fitting techniques through equation 23. Then, the energy-dependent function sps(E) is obtained to a high degree of accuracy for a single cell. After normalization, the energy dependent function sps(E) of one cell represents that of all the cells of the same detector.

Once the value for sps(E) is determined to the desired accuracy, the dual-energy signals as a function of the material composition of the subject is calculated through the equations $$D_H = \int sps_H(E) \times exp(-(\mu_b(E) \times b + \mu_s(E) \times s) dE \quad (25a)$$

and $$D_L = \int sps_L(E) \times exp(-(\mu_b(E) \times b + \mu_s(E) \times s) dE \quad (25b)$$

where $\mu_b(E)$ and $\mu_s(E)$ are the well-documented mass absorption coefficients for bone tissue and soft tissue, respectively. The mass surface densities b and s are assigned values that sufficiently cover the real range of the subject 12.

Another preferred method for constructing the quantitative explicit functions $D_L = D_L(b,s)$ and $D_H = D_H(b,s)$ is to conduct direct measurements of signals $D_L$ and $D_H$ at a number of selected b and s values. The number of data points for b and s is in the range of approximately 5 to approximately 30. The more data points data points that are used, the higher the accuracy of the results. However, the number of data points is limited by the acceptable amount of work. The entire functions $D_L = D_L(b,s)$ and $D_H = D_H(b,s)$ are obtained from the directly measured data points by using standard two-dimensional interpolation algorithms. After interpolation, there are from approximately 50 to approximately 50,000 data points for b and s. The interpolation in this case is valid because the functions $D_L = D_L(b,s)$ and $D_H = D_H(b,s)$ are continuous, smooth, and monotonous.

Figure 13A:
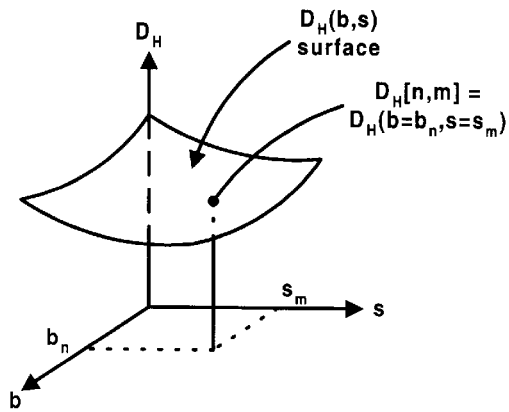
FIGS. 13a to 13d is a graphically representation of a method for inverting the nonlinear dual-energy equation systems.
Figure 13B:
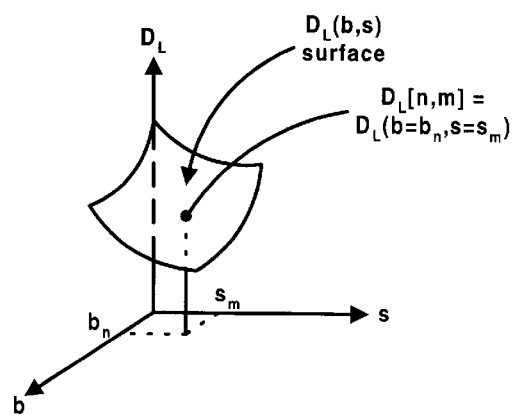
Figure 13C:
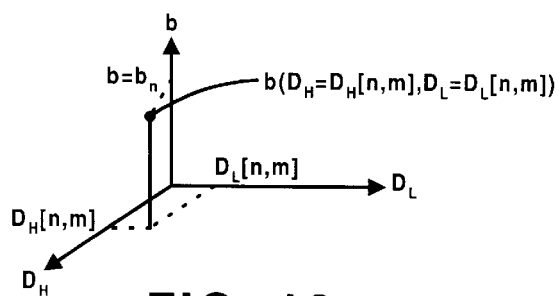
Figure 13D:
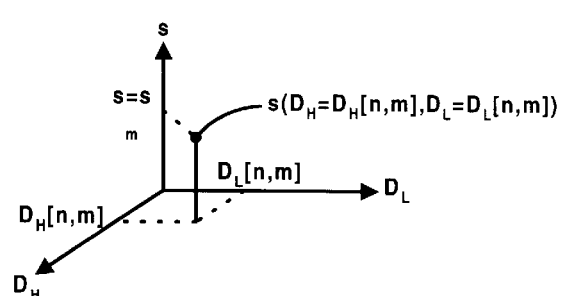

The second step is to determine the material composition images b and s as functions of the image pair $D_H$, $D_L$. The procedures for obtaining a simultaneous equation system for $b(D_H, D_L)$ and $s(D_H, D_L)$ are shown graphically in FIGS. 13*a* to 13*d*. To do so, the simultaneous equation pair 24*a*, 24*b* must be inverted. A preferred method of inversion is as follows: (1) as in FIGS. 13*a* and 13*b*, assign a pair of values in the desired range to b and s corresponding to one of the coordinate points in the (b,s) plane so that $b=b_n$, and $s=S_m$, where n=0,1,2 ... N, and m=0,1,2 ... M. Typical N and M values are in the range of between approximately 50 and approximately 5,000. The larger N and M, the higher the accuracy of the results. However, the largest values for N and M are limited by the available capacity of computer memory and computing speed. From the two numerical equations representing the three-dimensional surfaces $D_H(b,s)$ and $D_L(b,s)$, determine a pair of $D_H$ and $D_L$ values so that $D_H[n,m] = D_H(b=b_n, s=s_m)$ and $D_L[n,m] = D_L(b=b_n, s=s_m)$, where $D_H[n,m]$ and $D_L[n,m]$ are two specific real numbers, and (2) as in FIGS. 13*c* and 13*d*, replot the four numbers $D_H[n,m]$, $D_L[n,m]$, $b_n$, and $s_m$ to provide a pair of data points on the three-dimensional surfaces $b(D_H, D_L)$ and $s(D_H, D_L)$. The data point on the three-dimensional surface $b(D_H, D_L)$ is $D_H = D_H[n,m]$, $D_L = D_L[n,m]$, $b=b_n$, and the data point on the three-dimensional surface $s(D_H, D_L)$ is $D_H = D_H[n,m]$, $D_L = D_L[n,m]$, $s=s_m$. After going through all the $b=b_n$ values ($b_0, b_1, b_2, \ldots, b_N$) and all the $s=s_m$ values ($S_0, S_1, S_2, \ldots, S_M$), the essential part of the inversion task is complete. However, for the purpose of storing the inverted arrays $b=b(D_H, D_L)$ and $s=s(D_H, D_L)$, the step sizes of $D_H = D_H[n,m]$ and $D_L = D_L[n,m]$ must be adjusted. In the inverted space, $D_H$ and $D_L$ are basis coordinates. From the N×M data points, only J data points are selected for $D_H$ and only K data points are selected for $D_L$, where J and K are approximately in the same range as N and M. In the final form after the second step, two two-dimensional arrays are obtained and stored: $b = b(D_H, D_L)$ and $s=s(D_H, D_L)$, where $D_H = D_H[j]$, $D_L = D_L[k]$; j=0,1,2, ...,J, $D_H[j] > D_H[j+1]$ and k=0,1,2, ...,K, $D_L[k] > D_L[k+1]$. Two additional one-dimensional arrays $D_H[j]$ and $D_L[k]$ are also stored. Arrays $D_H[j]$ and $D_L[k]$ are saved so that accuracy as high as real number calculations can provide is maintained.

Note the important theoretical foundation for the numerical inversion process. It can be generally proven in mathematics that a unique solution always exists for the dual-energy fundamental nonlinear equation system in its original form with its parameters in the physical range of x-ray imaging as specified above. The most important feature is that each equation in the dual-energy fundamental equation system in its original form is continuous and uniformly monotonous with respect to both variables b and s. Because of the uniqueness of the solution, the above inversion process is meaningful and can always give a correct solution.

The third step is to find the desired results from the input data according to the established equations. The desired values for b and s at each cell location is determined by inserting the available data pair $(D_H, D_L)$ into the numerical equations of step 2. Conversely, the desired values for $D_H$, $D_L$, or only one of them if only one is needed, at each discrete cell location is determined by inserting the available data pair (b,s) into the numerical equations of step 1.

The final step is to maintain the accuracy of the values for b and s in order to maintain a continuous domain function. This means that the accuracy of the calculations is maintained at a level as high as the result that would be given by real number analytical calculations. Because of the digital nature of computers, the data arrays stored in computers must have finite steps, which are assumed here to have integer values as indices of the real number arrays. The following procedures ensure elimination of the errors in connection with these finite steps in data processing.

In step 1, in the process of constructing the equation pair for $D_H[n,m] = D_H(b=b_n, s=s_m)$ and $D_L[n,m] = D_L(b=b_n, s=s_m)$, for each pair of values of $b_n$ and $s_m$, the $D_H[n,m]$ and $D_L[n,m]$ are measured or calculated to an accuracy of real numbers. $D_H[n,m]$ and $D_L[n,m]$ are stored in computer as real number arrays.

In step 2, the inversion process, including replotting in $D_H$ space and $D_L$ space, introduces no errors due to the data processing. The step sizes can be changed without losing any accuracy as long as values for $D_H=D_H[j]$ are selected that are exactly equal to one of the $D_H[n,m]$ values that satisfies the condition $D_H[j-1] > D_H[j] > D_H[j+1]$, and values for $D_L=D_L[k]$ are selected that are exactly equal to one of the $D_L[n,m]$ values that satisfies the condition $D_L[k-1] > D_L[k] > D_L[k+1]$.

In step 3, for each measured dual-energy signal data pair $(D_{HEX}, D_{LEX})$, first to find out the closest j and k values according to the criteria: $D_H[j] \geq D_{HEX} \geq D_H[j+1]$ and $D_L[k] \geq D_{LEX} \geq D_L[k+1]$. From the index values j and k, the closest b and s are first determined as $b_0=b_0(D_H[j], D_L[k])$ and $s_0=s_0(D_H[j], D_L[k])$. The following equations give b and s values to an accuracy as high as real number calculations can provide:

$$b = b_0(D_H[j], D_L[k]) + [\partial b(D_H, D_L)/\partial D_L]_{DH=DH[j];DL=DL[k]} \times \quad (26a)$$

$$(D_{LEX} - D_L[k]) + [\partial b(D_H,D_L)/\partial D_H]_{DH=DH[j];DL=DL[k]} \times$$

$$(D_{HEX} - D_H[j]) + \text{higher order terms}$$

and $$s = s_0(D_H[j],D_L[k]) + [\partial s(D_H,D_L)/\partial D_L]_{DH=DH[j];DL=DL[k]} \times \quad (26b)$$

$$(D_{LEX} - D_L[k]) + [\partial s(D_H,D_L)/\partial D_H]_{DH=DH[j];DL=DL[k]} \times$$

$$(D_{HEX} - D_H[j]) + \text{higher order terms}$$

where the values for the higher order terms are found in standard calculus textbooks.

Also in step 3, if the image pair $D_H$ and $D_L$ from a given material composition data pair $(b_{ex}, s_{ex})$ is to be found, $D_H$ and $D_L$ is obtained to an accuracy of real numbers by using similar standard Taylor expressions.

Thus, the procedures described above provide methods for directly solving the nonlinear dual-energy x-ray imaging fundamental equation systems in its original form with arbitrary bremsstrahlung spectra at an accuracy as high as using real number analytical calculations can provide. The following is a list of possible further variations in the embodiments:

(1) According to current theory, within the energy range of diagnostic x-rays, any two materials with different mass absorption coefficients with low to medium atomic numbers can be used to represent the x-ray absorption of the material composition of the image subject.

(2) It is not necessary that 100% of the primary x-rays be transmitted through the beam selector to the selected locations. When the beam selector is an x-ray-absorbent material with holes, the transmission is defined as the ratio of the x-ray intensity at the exit of the hole to the x-ray intensity at the entrance of the hole. One example when the transmission is less than 100% is when there is an amount of substance present in the holes. Another example is when part of the hole wall, especially the edge of the wall, blocks a portion of primary x-rays to the rear detector assembly when the x-ray source has a finite size. When the x-ray transmission is less than 100% but greater than 0, all of the above-described dual-energy methods still hold true, with the following difference. When the x-ray transmission less than 100% through the holes, the absorption of x-rays in the holes should be factored into the spectral sensitivity function Sr(E) of the rear detector, which is obtained through calibration.

(3) There are several further variations of the first special case of the first embodiment. For example, when the front detector assembly includes a front low-energy detector, an energy filter, and an high-energy detector, high spatial resolution dual-energy x-ray imaging can be conducted with the scatter removed for the first special case. All of the variations based on the first special case, in parallel with the three embodiments illustrated in FIG. 5, FIG. 9, and FIG. 11 and described above in detail, are essentially a simplified or degenerated version of the above three embodiments and are contemplated by this invention.

(4) There are several further variations of the second special case of the first embodiment. When the transmission of x-rays through the holes is 100%, all of the variations based on the second special case, in parallel with the three embodiments illustrated in FIGS. 5, 9, and 11 and described above in detail, are essentially an equivalent version of the above three embodiments and are contemplated by this invention.

When the transmission of x-rays through the holes is less than 100%, to eliminate scatter by using a beam selector moved to and away from a detector assembly, dual-energy x-ray imaging methods must be used. In this case, acquiring the data when the beam selector is in front of and not in front of the detector assembly is essentially equivalent to the process of acquiring the data when the beam selector and the detector assembly are at a fixed position as illustrated in FIGS. 5, 9, and 11 and described above in detail for the above three embodiments. For example, the process of acquiring data at two different x-ray energy spectra ($\Phi_{OH}(E)$ and $\Phi_{OL}(E)$) when the beam selector is in front of and not in front of a single detector as illustrated in FIG. 7 is essentially equivalent to the second embodiment described above. When the detector assembly is composed of a low-energy x-ray detector, an x-ray energy filter and an high-energy detector, the process of acquiring data at an x-ray energy spectrum $\Phi_0(E)$, the process of acquiring data when the beam selector is in front of and not in front of the detector assembly is essentially equivalent to the third embodiment described above.

(5) The entire process of constructing $(D_H,D_L)$ pair as functions of (b,s) may be carried out using a functional scale or grid steps other than a linear scale, such as a logarithmic scale.

(6) Some well-established computation tools, such as sorting algorithms or database procedures, can be used to carry out the inversion process described above. The use of any such software package to conduct the above-described inversion process is contemplated by the present invention.

(7) In the methods for eliminating scatter, in some cases, currently already-known dual-energy x-ray data decomposition methods can also be used for obtaining the low-resolution front detector image Dfpl or image pair $D_{fHp}$, and $D_{fLP1}$. These methods can be characterized as solving the nonlinear fundamental dual-energy x-ray equation systems through a linearization approximation method with corrections for beam hardening effects. The correction includes second-order approximations. However, in doing so, the results will be limited by the accuracy and capability inherent to these approximation methods used in the process. Using any currently available dual-energy methods as a data decomposition method in eliminating scatter process is contemplated by the present invention.

(8) All of the steps described above, including the data decomposition method and the scatter elimination method, can be combined together to various degrees, from combining any two steps to combining all the steps into one procedure. For example, equation pair 18a, 18b and equation pair 17a, 17b can be combined, with minor modifications, into a larger four-equation system and solved using the previously determined ($D_{rH}$,$D_{rL}$) to find ($D_{fHP}$, $D_{fLP}$) without explicitly determining (b,s). One way of doing so is to construct a pair of quantitative relationships $D_{fHP}$= ($D_{rH}$,$D_{rL}$) and $D_{fLP}$=($D_{rH}$,$D_{rL}$) in a data base and storing them. From the measured data pair ($D_{rH}$,$D_{rL}$) of the rear detector assembly, a new data pair ($D_{fHP}$,$D_{fLP}$) of the front detector assembly can be directly found. Any such combination methods are contemplated by the present invention.

The foregoing descriptions of the preferred embodiments of the invention have been presented for the purpose of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A two-dimensional x-ray imaging system for taking images of a subject, said system comprising:
   (a) in physical sequence from front to back, an x-ray source, a front two-dimensional x-ray detector assembly, a beam selection means, and a rear two-dimensional x-ray detector assembly, said subject being located between said x-ray source and said front detector assembly;
   (b) said x-ray source being adapted to emit x-rays for passage through said subject, said x-rays including primary x-rays having their direction of travel unaltered by interaction with said subject and said x-rays including scatter x-rays having their direction of travel altered by interaction with said subject;
   (c) said front detector assembly receiving said primary x-rays and said scatter x-rays;
   (d) said beam selection means permitting said rear detector assembly to receive said primary x-rays and preventing said rear detector assembly from receiving substantially all of said scatter x-rays; and
   (e) said rear detector assembly receiving substantially only said primary x-rays passing through said beam selection means.

2. The x-ray imaging system of claim 1 wherein said x-ray source is adapted to emit x-rays with an average energy in the range of from approximately 20 keV to approximately 150 keV.

3. The x-ray imaging system of claim 1 wherein said front detector assembly includes a front detector array having a plurality of x-ray-sensitive detector cells arranged in a substantially rectangular matrix with from approximately 128 to approximately 16,384 detector cells on a side.

4. The x-ray imaging system of claim 1 wherein said beam selection means is substantially comprised of an x-ray-absorbent material having a plurality of holes, the axes of said holes being parallel to the direction of travel of said primary x-rays.

5. The x-ray imaging system of claim 4 wherein the thickness of said beam selection means is between approximately 0.5 cm and 20 cm.

6. The x-ray imaging system of claim 4 wherein a radial cross-sectional dimension of said holes is between approximately 0.5 mm and approximately 10 mm with a pitch of between approximately 2 mm and approximately 50 mm.

7. The x-ray imaging system of claim 4 wherein said holes have an x-ray transmission of less than 100% and greater than 0%.

8. The x-ray imaging system of claim 1 wherein said rear detector assembly includes a rear detector array having a plurality of x-ray-sensitive detector cells arranged in a substantially rectangular matrix with from approximately 8 to approximately 1,024 detector cells on a side and said x-ray source is adapted to emit two x-ray pulses of different average energies, one of said pulses having an average x-ray energy in the range of from approximately 20 keV to approximately 100 keV and another of said pulses having an average x-ray energy in the range of from approximately 30 keV to approximately 500 keV.

9. The x-ray imaging system of claim 1 wherein said rear detector assembly includes, in physical sequence, a rear low-energy detector, a rear x-ray energy spectral filter, and a rear high-energy detector, said rear low-energy detector including a plurality of x-ray-sensitive detector cells arranged in a substantially rectangular matrix with from approximately 8 to approximately 1,024 detector cells on a side, said rear high-energy detector including a plurality of x-ray-sensitive detector cells, the arrangement and quantity of said rear high-energy detector cells being substantially the same as the arrangement and quantity of said rear low-energy detector cells.

10. The x-ray imaging system of claim 1 wherein said front detector assembly includes a front detector array having a plurality of x-ray-sensitive detector cells arranged in a substantially rectangular matrix with from approximately 128 to approximately 16,384 detector cells on a side.

11. The x-ray imaging system of claim 1 wherein said front detector assembly includes, in physical sequence, a front low-energy detector, a front x-ray energy spectral filter, and a front high-energy detector, said front low-energy detector including a plurality of x-ray-sensitive detector cells arranged in a substantially rectangular matrix with from approximately 128 to approximately 16,384 detector cells on a side, said front high-energy detector including a plurality of x-ray-sensitive detector cells, the arrangement and quantity of said front high-energy detector cells being substantially the same as the arrangement and quantity of said front low-energy detector cells.

12. A two-dimensional x-ray imaging system for taking images of a subject, said system comprising:
   (a) in physical sequence from front to back, an x-ray source, a front two-dimensional x-ray detector assembly, a beam selection means, and a rear two-dimensional x-ray detector assembly, said subject being located between said x-ray source and said front detector assembly;
   (b) said x-ray source being adapted to emit x-rays with an energy in the range of from approximately 10 keV to approximately 500 keV for passage through said subject, said x-rays including primary x-rays having their direction of travel unaltered by interaction with said subject and said x-rays including scatter x-rays having their direction of travel altered by interaction with said subject;
   (c) said front detector assembly receiving said primary x-rays and said scatter x-rays;
   (d) said beam selection means permitting said rear detector assembly to receive said primary x-rays and preventing said rear detector assembly from receiving substantially all of said scatter x-rays;

(e) said beam selection means being substantially comprised of an x-ray-absorbent material having a plurality of holes, the axes of said holes being parallel to said directions of travel of said primary x-rays; and (f) said rear detector assembly receiving substantially only said primary x-rays passing through said beam selection means.

13. The x-ray imaging system of claim 12 wherein said front detector assembly includes a front detector array having a plurality of x-ray-sensitive detector cells arranged in a substantially rectangular matrix with from approximately 128 to approximately 16,384 cells on a side, said rear detector assembly includes a rear detector array having a plurality of x-ray-sensitive detector cells arranged in a substantially rectangular matrix with from approximately 8 to approximately 1,024 cells on a side, and said x-ray source is adapted to emit two x-ray pulses of different average energies, one of said pulses having an average x-ray energy in the range of from approximately 20 keV to approximately 100 keV and another of said pulses having an average x-ray energy in the range of from approximately 30 keV to approximately 500 keV.

14. The x-ray imaging system of claim 12 wherein said front detector assembly includes a plurality of x-ray-sensitive detector cells arranged in a substantially rectangular matrix with from approximately 128 to approximately 16,384 detector cells on a side and said rear detector assembly includes, in physical sequence, a rear low-energy detector, a rear x-ray energy spectral filter, and a rear high-energy detector, said rear low-energy detector including a plurality of rear low-energy x-ray-sensitive detector cells arranged in a substantially rectangular matrix with from approximately 8 to approximately 1,024 detector cells on a side and said rear high-energy detector including a plurality of x-ray-sensitive detector cells, the arrangement and quantity of said rear high-energy detector cells being substantially the same as the arrangement and quantity of said rear low-energy detector cells.

15. The x-ray imaging system of claim 14 wherein said front detector assembly includes, in physical sequence, a front low-energy detector, a front x-ray energy spectral filter, and a front high-energy detector, said front low-energy detector including a plurality of front low-energy x-ray-sensitive detector cells arranged in a substantially rectangular matrix with from approximately 128 to approximately 16,384 detector cells on a side and said front high-energy detector including a plurality of front high-energy x-ray-sensitive detector cells, the arrangement and quantity of said front high-energy detector cells being substantially the same as the arrangement and quantity of said front low-energy detector cells.

16. The x-ray imaging system of claim 12 wherein a radial cross-sectional dimension of said holes is between approximately 0.5 mm and approximately 10 mm with a pitch of between approximately 2 mm and approximately 50 mm.

17. The x-ray imaging system of claim 12 wherein the thickness of said beam selection means is between approximately 0.5 cm and approximately 20 cm.

18. A two-dimensional x-ray imaging system for taking images of a subject, said system comprising:

(a) an x-ray source adapted to emit x-rays for passage through said subject, said x-rays including primary x-rays having their direction of travel unaltered by interaction with said subject and said x-rays including scatter x-rays having their direction of travel altered by interaction with said subject;

(b) a two-dimensional x-ray detector;

(c) said subject being located between said x-ray source and said detector;

(c) a beam selection means for physically separating said primary x-rays from said scatter x-rays, said beam selection means having a blocking position wherein said detector is permitted to receive said primary x-rays but prevented from receiving substantially all of said scatter x-rays and a transmissive position wherein said detector is permitted to receive said primary x-rays and said scatter x-rays.

19. The x-ray imaging system of claim 18 wherein said x-ray source is adapted to emit x-rays with an average energy in the range of from approximately 20 keV to approximately 150 keV.

20. The x-ray imaging system of claim 18 wherein said detector includes a detector array having a plurality of x-ray-sensitive detector cells arranged in a substantially rectangular matrix with from approximately 128 to approximately 16,384 detector cells on a side.

21. The x-ray imaging system of claim 18 wherein said beam selection means is mechanically moved between said blocking position and said transmissive position.

22. The x-ray imaging system of claim 18 wherein said beam selection means is substantially comprised of an x-ray-absorbent material having a plurality of holes, the axes of said holes being parallel to the direction of travel of said primary x-rays.

23. The x-ray imaging system of claim 22 wherein the thickness of said beam selection means is between approximately 0.5 cm and approximately 20 cm.

24. The x-ray imaging system of claim 22 wherein a radial cross-sectional dimension of said holes is between approximately 0.5 mm and approximately 10 mm with a pitch of between approximately 2 mm and approximately 50 mm.

25. The x-ray imaging system of claim 22 wherein said holes have an x-ray transmission of less than 100% and greater than 0%.

26. A method for taking a two-dimensional x-ray image of a subject using a two-dimensional x-ray imaging system, said subject being composed substantially of two materials, $M_A$ and $M_B$, that interact differently with x-rays and having a two-dimensional projection mass density A for said material $M_A$ and a two-dimensional projection mass density B for said material $M_B$, said imaging system including, in physical sequence from front to back, an x-ray source, a front two-dimensional x-ray detector having a plurality of detection locations identified by the notation (x,y), a beam selection means, and a rear detector assembly, said subject being between said x-ray source and said front detector, said x-ray source being adapted to emit x-rays for passage through said subject, said x-rays including primary x-rays having their direction of travel unaltered by interaction with said subject and said x-rays including scatter x-rays having their direction of travel altered by interaction with said subject, said rear detector assembly including a rear low-energy two-dimensional x-ray detector having a plurality of selected rear low-energy detection locations identified by the notation (i,j), a rear x-ray energy spectral filter, and a rear high-energy two-dimensional x-ray detector having a number of selected rear high-energy detection locations equal to said plurality of selected rear low-energy detection locations, said beam selection means blocking the passage of substantially all of said scatter x-rays to said selected rear low-energy detection locations and said selected rear high-energy detection locations and permitting the passage of said primary x-rays to said selected rear low-energy detection locations and said selected rear high-energy detection locations, said selected rear low-energy detection locations and said selected rear high-energy detection locations receiving only primary x-rays, and selected front detection locations being those of said front detection locations intersected by x-ray projection lines extending from said x-ray source to said selected rear low-energy detection locations and said selected rear high-energy detection locations, said selected front detection locations being identified by the notation (x(i),y(j)), said method comprising:

(a) illuminating said subject with said x-rays;

(b) acquiring a high-resolution image $I_{fh}$ from said front detection locations and processing said image $I_{fh}$ to normalize it and to subtract dark signals, yielding an image $D_{fh}$, which is composed of said primary x-rays and said scatter x-rays;

(c) producing, from said image $D_{fh}$, a low-resolution image $D_{fl}$ representing said selected front detection locations;

(d) acquiring a low-resolution image $I_{rHl}$ from said selected rear high-energy detection locations and processing said image $I_{rHl}$ to normalize it and to subtract dark signals, yielding an image $D_{rHl}$ composed of substantially only said primary x-rays;

(e) acquiring a low-resolution image $I_{rLl}$ from said selected rear low-energy detection locations and processing said image $I_{rLl}$ to normalize it and to subtract dark signals, yielding an image $D_{rLl}$ composed of substantially only said primary x-rays;

(f) calculating a low-resolution primary x-ray image $D_{fPl}$ at said front detector from a low-resolution dual-energy primary x-ray imaging pair composed of said image $D_{rHl}$ and said image $D_{rLl}$;

(g) calculating a low-resolution scatter x-ray image $D_{fSl}$ at said front detector by subtracting said low-resolution primary x-ray image $D_{fPl}$ from said low-resolution image $D_{fl}$;

(h) calculating a high-resolution scatter image $D_{fSh}$ by extending said low-resolution scatter image $D_{fSl}$ to the entire image area of said front detector through interpolation; and (i) calculating a high-resolution primary x-ray image $D_{fPh}$ by subtracting said high-resolution scatter image $D_{fSh}$ from said high-resolution image $D_{fh}$;

(j) whereby said high-resolution primary x-ray image $D_{fPh}$ is a two-dimensional image of said subject at said front detector after said scatter x-rays have been substantially eliminated, said image $D_{fPh}$ having a spatial resolution substantially equal to the highest spatial resolution available from said front detector.

27. The method for taking a two-dimensional x-ray image of claim 26 wherein said low-resolution primary x-ray image $D_{fPl}$ at said front detector is calculated by:

(a) solving a nonlinear equation system of said low-resolution dual-energy primary x-ray image pair $D_{rHl}$, $D_{rLl}$ for said selected projection mass densities A(i,j) and B(i,j), wherein said equation system is $D_{rHl}(i,j)=\int [\Phi_0(E)\times\exp(-(\mu_A(E)\times A(i,j)+\mu_B(E)\times B(i,j)))]\times S_{rH}(E) dE$ and $D_{rLl}(i,j)=\int [\Phi_0(E)\times\exp(-(\mu_A(E)\times A(i,j)+\mu_B(E)\times B(i,j)))]\times S_{rL}(E)dE$; and (b) inserting said A(i,j) and B(i,j) solutions into the equation for said image of said front detector $D_{fPl}(x(i),y(j))=\int [\Phi_0(E)\times S_f(E)]\times\exp(-(\mu_A(E)\times A(i,j)+\mu_B(E)\times B(i,j)))dE$, wherein $\Phi_0(E)$ is the energy spectrum of said x-rays, $\mu_A(E)$ is the mass absorption coefficient of said material $\mu_A$ having selected projection density A(i,j), $\mu_B(E)$ is the mass absorption coefficient of said material $\mu_B$ having selected projection density B(i,j), $S_f(E)$ is the spectral sensitivity of said front detection locations, $S_{rH}(E)$ is the spectral sensitivity of said selected rear high-energy detection locations, and $S_{rL}(E)$ is the spectral sensitivity of said selected rear low-energy detection locations.

28. The method for taking a two-dimensional x-ray image of claim 26 wherein said low-resolution image at said front detector $D_{fPl}(x(i),y(j))$ is calculated from said image pair $D_{rHl}(i,j)$, $D_{rLl}(i,j)$ by using a direct quantitative relationship $D_{fPl}(x(i),y(j))=D_{fPl}(D_{rHl}(i,j),D_{rL}(i,j))$.

29. The method for taking a two-dimensional x-ray image of claim 26 wherein said low-resolution image at said front detector $D_{fPl}(x(i),y(j))$ is calculated from said image pair $D_{rHl}(i,j)$, $D_{rLl}(i,j)$ by using a linearization approximation method with correction for beam hardening effects.

30. A method for taking a two-dimensional x-ray image of a subject using a two-dimensional x-ray imaging system, said subject being composed substantially of two materials, $M_A$ and $M_B$, that interact differently with x-rays and having a two-dimensional projection mass density A for said material $M_A$ and a two-dimensional projection mass density B for said material $M_B$, said imaging system including, in physical sequence from front to back, an x-ray source, a front two-dimensional x-ray detector having a plurality of front detection locations identified by the notation (x,y), a beam selection means, and a rear two-dimensional x-ray detector having a plurality of selected rear detection locations identified by the notation (i,j), said subject being between said x-ray source and said front detector, said x-ray source being adapted to emit x-rays at two different average energy levels for passage through said subject, said x-rays including primary x-rays having their direction of travel unaltered by interaction with said subject and said x-rays including scatter x-rays having their direction of travel altered by interaction with said subject, said beam selection means blocking the passage of substantially all of said scatter x-rays to said selected rear detection locations and permitting the passage of said primary x-rays to said selected rear detection locations, said selected rear detection locations receiving only primary x-rays, and selected front detection locations being those of said front detection locations intersected by x-ray projection lines extending from said x-ray source to said selected rear detection locations, said selected front detection locations being identified by the notation (x(i),y(j)), said method comprising:

(a) illuminating said subject with x-rays of a first average energy level H;

(b) acquiring a high-resolution image $I_{fHh}$ from said front detection locations and processing said image $I_{fHh}$ to normalize it and to subtract dark signals, yielding an image $D_{fHh}$ which is composed of primary x-rays and scatter x-rays;

(c) producing, from said image $D_{fHh}$, a low-resolution image $D_{fHl}$ representing said selected front detection locations;

(d) acquiring a low-resolution image $I_{rHl}$ from said selected rear detection locations and processing said image $I_{rHl}$ to normalize it and to subtract dark signals, yielding an image $D_{rHl}$ composed of substantially only said primary x-rays;

(e) illuminating said subject with x-rays of a second average energy level L;

(f) acquiring a high-resolution image $I_{fLh}$ from said front detection locations and processing said image $I_{fLh}$ to normalize it and to subtract dark signals, yielding an image $D_{fLh}$ which is composed of primary x-rays and scatter x-rays;

(g) producing, from said image $D_{fLh}$, a low-resolution image $D_{fLl}$ representing said selected front detection locations;

(h) acquiring a low-resolution image $I_{rLl}$ from said selected rear detection locations and processing said image $I_{rLl}$ to normalize it and to subtract dark signals, yielding an image $D_{rLl}$ composed of substantially only said primary x-rays;

(i) calculating a pair of low-resolution primary x-ray images $D_{fLPl}$ and $D_{fHPl}$ at said front detector from a low-resolution dual-energy primary x-ray imaging pair composed of said image $D_{rHl}$ and said image $D_{rLl}$;

(j) calculating a low-resolution scatter x-ray image $D_{fLSl}$ at said front detector by subtracting said image $D_{fLPl}$ from said image $D_{rLl}$ and calculating a low-resolution scatter x-ray image $D_{fHSl}$ at said front detector by subtracting said image $D_{fHPl}$ from said image $D_{rHl}$;

(k) calculating a high-resolution scatter image $D_{fLSh}$ by extending said low-resolution scatter image $D_{fLSl}$ to the entire image area of said front detector through interpolation and calculating a high-resolution scatter image $D_{fHSh}$ by extending said low-resolution scatter image $D_{fHSl}$ to said entire image area of said front detector through interpolation; and (l) calculating a high-resolution primary x-ray image $D_{fHPh}$ at said front detector by subtracting said image $D_{fHSh}$ from said image $D_{fHh}$ and calculating a high-resolution primary x-ray image $D_{fLPh}$ at said front detector by subtracting said image $D_{fLSh}$ from said image $D_{fLh}$;

(m) whereby said images $D_{fHPh}$ and $D_{fLPh}$ form a high-resolution, two-dimensional, dual-energy primary x-ray image pair $D_{fHPh}$, $D_{fLPh}$ of said subject at said front detector after said scatter x-rays have been substantially eliminated, said image pair having a spatial resolution substantially equal to the highest spatial resolution available from said front detector.

31. The method for taking a two-dimensional x-ray image of claim 30 wherein said two-dimensional projection mass densities A and B along said projection lines are calculated from said image pair $D_{fHPh}$, $D_{fLPh}$, whereby said projection mass densities A and B have a resolution substantially equal to the highest resolution available from said front detector.

32. The method for taking a two-dimensional x-ray image of claim 30 wherein said image pair $D_{fHPl}$, $D_{fLPl}$ is calculated by:

(a) solving a nonlinear equation system image pair for said projection mass densities $A(i,j)$ and $B(i,j)$, wherein said equation system is $D_{rHl}(i,j)=\int[\Phi_{0H}(E)\times\exp(-(\mu_A(E)\times A(i,j)+\mu_B(E)\times B(i,j))))]\times S_r(E)dE$ and $D_{rLl}(i,j)=\int[\Phi_{0L}(E)\times\exp(-(\mu_A(E)\times A(i,j)+\mu_B(E)\times B(i,j))))]\times S_r(E)dE$; and (b) inserting said $A(i,j)$ and $B(i,j)$ solutions into the equations for said image pair according to $D_{fLPl}(x(i),y(j))=\int[\Phi_{0L}(E)\times S_f(E)]\times\exp(-(\mu_A(E)\times A(i,j)+\mu_B(E)\times B(i,j)))dE$ and $D_{fHPl}(x(i),y(j))=\int[\Phi_{0H}(E)\times S_f(E)]\times\exp(-(\mu_A(E)\times A(i,j)+\mu_B(E)\times B(i,j)))dE$, wherein $\Phi_{0L}(E)$ is the energy spectrum of said x-rays of average energy level L, $\Phi_{0H}(E)$ is the energy spectrum of said x-rays of average energy level H, $\mu_A(E)$ is the mass absorption coefficient of said material $M_A$ having selected projection density $A(i,j)$, $\mu_B(E)$ is the mass absorption coefficient of said material $M_B$ having selected projection density $B(i,j)$, $S_f(E)$ is the spectral sensitivity of said front detection locations, and $S_r(E)$ is the spectral sensitivity of said selected rear detection locations.

33. The method for taking a two-dimensional x-ray image of claim 30 wherein said image pair $D_{fHPl}(x(i),y(j))$, $D_{fLPl}(x(i),y(j))$ is calculated from said image pair $D_{rHl}(i,j)$, $D_{rLl}(i,j)$ by using direct quantitative relationships $D_{fHPl}((x(i),y(j))=D_{fHPl}(D_{rHl}(i,j)), D_{rLl}(i, j))$ and $D_{fLPl}(x(i),y(j))=D_{fLPl}(D_{rHl}(i,j),D_{rLl}(i,j))$.

34. The method for taking a two-dimensional x-ray image of claim 30 wherein said image pair $D_{fHPl}(x(i),(j))$, $D_{fLPl}(x(i),y(j))$ is calculated from said image pair $D_{rHl}(i,j)$, by solving a dual-energy primary x-ray imaging equation system by using a linearization approximation method with correction for beam hardening effects.

35. A method for taking a two-dimensional x-ray image of a subject using a two-dimensional x-ray imaging system, said subject being composed substantially of two materials, $M_A$ and $M_B$, that interact differently with x-rays and having a two-dimensional projection mass density A for said material $M_A$ and a two-dimensional projection mass density B for said material $M_B$, said imaging system including, in physical sequence from front to back, an x-ray source, a front detector assembly, a beam selection means, and a rear detector assembly, said subject being between said x-ray source and said front detector assembly, said x-ray source being adapted to emit x-rays for passage through said subject, said x-rays including primary x-rays having their direction of travel unaltered by interaction with said subject and said x-rays including scatter x-rays having their direction of travel altered by interaction with said subject, said front detector assembly including a front low-energy two-dimensional x-ray detector having a plurality of front low-energy detection locations identified by the notation (x,y), a front x-ray energy spectral filter, and a front high-energy two-dimensional x-ray detector having a number of front high-energy detection locations equal to said plurality of front low-energy detection locations, said rear detector assembly including a rear low-energy two-dimensional x-ray detector having a plurality of selected rear low-energy detection locations identified by the notation (i,j), a rear x-ray energy spectral filter, and a rear high-energy two-dimensional x-ray detector having a number of selected rear high-energy detection locations equal to said plurality of selected rear low-energy detection locations, said beam selection means blocking the passage of substantially all of said scatter x-rays to said selected rear low-energy detection locations and said selected rear high-energy detection locations and permitting the passage of said primary x-rays to said selected rear low-energy detection locations and said selected rear high-energy detection locations, said selected rear low-energy detection locations and said selected rear high-energy detection locations receiving only primary x-rays, selected front high-energy detection locations being those of said front high-energy detection locations intersected by x-ray projection lines extending from said x-ray source to said selected rear low-energy detection locations and said selected rear high-energy detection locations, selected front low-energy detection locations being those of said front low-energy detection locations intersected by said x-ray projection lines, said selected front high-energy detection locations and said selected front low-energy detection locations being identified by the notation (x(i),y(j)), said method comprising:

(a) illuminating said subject with said x-rays;

(b) acquiring a high-resolution image $I_{fLh}$ from said front low-energy detection locations and processing said image $I_{fLh}$ to normalize it and to subtract dark signals, yielding an image $D_{fLh}$, which is composed of said primary x-rays and said scatter x-rays;

(c) producing, from said image $D_{fLh}$, a low-resolution image $D_{fLl}$ representing said selected front low-energy detection locations;

(d) acquiring a high-resolution image $I_{fHh}$ from said front high-energy detection locations and processing said image $I_{fHh}$ to normalize it and to subtract dark signals, yielding an image $D_{fHh}$, which is composed of said primary x-rays and said scatter x-rays;

(e) producing, from said image $D_{fHh}$, a low-resolution image $D_{fHl}$ representing said selected front high-energy detection locations;

(f) acquiring a low-resolution image $I_{rHl}$ from said selected rear high-energy detection locations and processing said image $I_{rHl}$ to normalize it and to subtract dark signals, yielding an image $D_{rHl}$ composed of substantially only said primary x-rays;

(g) acquiring a low-resolution image $I_{rLl}$ from said selected rear low-energy detection locations and processing said image $I_{rLl}$ to normalize it and to subtract dark signals, yielding an image $D_{rLl}$ composed of substantially only said primary x-rays;

(h) calculating a pair of low-resolution primary x-ray images $D_{fHPl}$ at said front high-energy detector and $D_{fLPl}$ at said front low-energy detector from a low-resolution dual-energy primary x-ray imaging pair composed of said image $D_{rHl}$ and said image $D_{rLl}$;

(i) calculating a low-resolution scatter x-ray image $D_{fHSl}$ at said front high-energy detector by subtracting said image $D_{fHPl}$ from said image $D_{fHl}$ and calculating a low-resolution scatter x-ray image $D_{fLSl}$ at said front low-energy detector by subtracting said image $D_{fLPl}$ from said image $D_{fLl}$;

(j) calculating a high-resolution scatter image $D_{fHSh}$ by extending said low-resolution scatter image $D_{fHSl}$ to the entire image area of said front high-energy detector through interpolation and calculating a high-resolution scatter image $D_{fLSh}$ by extending said low-resolution scatter image $D_{fLSl}$ to the entire image area of said front low-energy detector through interpolation; and (k) calculating a high-resolution primary x-ray image $D_{fHPh}$ at said front detector assembly by subtracting said image $D_{fHSh}$ from said image $D_{fHh}$ and calculating a high-resolution primary x-ray image $D_{fLPh}$ at said front detector assembly by subtracting said image $D_{fLSh}$ from said image $D_{fLh}$;

whereby said images $D_{fHPh}$ and $D_{fLPh}$ form a high-resolution, two-dimensional, dual-energy primary x-ray image pair $D_{fHPh}$, $D_{fLPh}$ of said subject at said at said front detector assembly after said scatter x-rays have been substantially eliminated, said image pair having a spatial resolution substantially equal to the highest spatial resolution available from said front detector assembly.

36. The method for taking a two-dimensional x-ray image of claim 35 wherein said two-dimensional projection mass densities A and B along said projection lines are calculated from said image pair $D_{fHPh}$, $D_{fLPh}$, whereby said projection mass densities A and B have a resolution substantially equal to the highest resolution available from said front detector.

37. The method for taking a two-dimensional x-ray image of claim 35 wherein said pair of low-resolution images of said front high-energy detector $D_{fHPl}(x(i),y(j))$ and said front low-energy detector $D_{fLPl}(x(i),y(j))$ are calculated from said primary x-ray image pair at said rear high-energy detector $D_{rHl}(i,j)$ and said rear low-energy detector $D_{rLl}(i,j)$ by:

(a) solving a nonlinear equation system image pair for said projection mass densities $A(i,j)$ and $B(i,j)$, wherein said equation system is $D_{rLl}(i,j)=\int[\Phi_0(E)\times\exp(-(\mu_A(E)\times A(i,j)+\mu_B(E)\times B(i,j)))]\times S_{rL}(E)dE$ and $D_{rHl}(i,j)=\int[\Phi_0(E)\times\exp(-(\mu_A(E)\times A(i,j)+\mu_B(E)\times B(i,j)))]\times S_{rH}(E)dE$; and (b) inserting said $A(i,j)$ and $B(i,j)$ solutions into the equations for said image pair according to $D_{fHPl}(x(i),y(j))=\int[\Phi_0(E)\times S_{fH}(E)]\times\exp(-(\mu_A(E)\times A(i,j)+\mu_B(E)\times B(i,j)))dE$ and $D_{fLPl}(x(i),y(j))=\int[\Phi_0(E)\times S_{fL}(E)]\times\exp(-(\mu_A(E)\times A(i,j)+\mu_B(E)\times B(i,j)))dE$, wherein $\Phi_0(E)$ is the energy spectrum of said x-rays, $S_{rH}(E)$ is the spectral sensitivity of said selected rear high-energy detection locations, $S_{rL}(E)$ is the spectral sensitivity of said selected rear low-energy detection locations, $S_{fH}(E)$ is the spectral sensitivity of said selected front high-energy detection locations, $S_{fL}(E)$ is the spectral sensitivity of said selected front low-energy detection locations, $\mu_A(E)$ is the mass absorption coefficient of said material $M_A$ having selected projection density $A(i,j)$, and $\mu_B(E)$ is the mass absorption coefficient of said material $M_B$ having selected projection density $B(i,j)$.

38. The method for taking a two-dimensional x-ray image of claim 35 wherein said image pair $D_{fHPl}(x(i),y(j))$, $D_{fLPl}(x(i),y(j))$ is calculated from said image pair $D_{rHl}(i,j)$, $D_{rLl}(i,j)$ by using direct quantitative relationships $D_{fHPl}((x(i),y(j))=D_{fHPl}(D_{rHl}(i,j)), D_{rLl}(i,j))$ and $D_{fLPl}(x(i),y(j))=D_{fLPl}(D_{rHl}(i,j),D_{rLl}(i,j))$.

39. The method for taking a two-dimensional x-ray image of claim 35 wherein said image pair $D_{fHPl}(x(i),(j))$, $D_{fLPl}(x(i),y(j))$ is calculated from said image pair $D_{rHl}(i,j)$, $D_{rLl}(i,j)$ by solving a dual-energy primary x-ray imaging equation system by using a linearization approximation method with correction for beam hardening effects.

40. A method for taking a two-dimensional x-ray image of a subject using a two-dimensional x-ray imaging system, said subject being composed substantially of two materials, $M_A$ and $M_B$, that interact differently with x-rays and having a two-dimensional projection mass density A for said material $M_A$ and a two-dimensional projection mass density B for said material $M_B$, said imaging system including, in physical sequence from front to back, an x-ray source, a front two-dimensional x-ray detector having a plurality of front detection locations, a beam selection means, and a rear two-dimensional x-ray detector having a plurality of selected rear detection locations, said subject being between said x-ray source and said front detector, said x-ray source being adapted to emit x-rays for passage through said subject, said x-rays having an energy spectrum that can be approximated as having a single energy $E_0$, said x-rays including primary x-rays having their direction of travel unaltered by interaction with said subject and said x-rays including scatter x-rays having their direction of travel altered by interaction with said subject, said beam selection means blocking the passage of substantially all of said scatter x-rays to said selected rear detection locations and permitting the passage of said primary x-rays to said selected rear detection locations, said selected rear detection locations receiving only primary x-rays, and selected front detection locations being those of said front detection locations intersected by x-ray projection lines extending from said x-ray source to said selected rear detection locations, said selected front detection locations being identified by the notation $(x(i),y(j))$, said method comprising:

(a) illuminating said subject with said x-rays;

(b) acquiring a high-resolution image $I_{fh}$ from said front detection locations and processing said image $I_{fh}$ to normalize it and to subtract dark signals, yielding an image $D_{fh}$ which is composed of primary x-rays and scatter x-rays;

(c) producing, from said image $D_{fh}$, a low-resolution image $D_{fl}$ representing said selected front detection locations;

(d) acquiring a low-resolution image $I_{rl}$ from said selected rear detection locations and processing said image $I_{rl}$ to normalize it and to subtract dark signals, yielding an image $D_{rl}$ composed of substantially only said primary x-rays;

(e) calculating a low-resolution primary x-ray image $D_{fPl}$ at said front detector by multiplying said image $D_{rl}$ by a predetermined constant that is independent of said subject;

(f) calculating a low-resolution scatter x-ray image $D_{fSl}$ at said front detector by subtracting said image $D_{fPl}$ from said image $D_{fl}$;

(g) calculating a high-resolution scatter image $D_{fSh}$ by extending said low-resolution scatter image $D_{fSl}$ to the entire image area of said front detector through interpolation; and (h) calculating a high-resolution primary x-ray image $D_{fPh}$ at said front detector by subtracting said image $D_{fSh}$ from said image $D_{fh}$;

(i) whereby said image $D_{fPh}$ is a high-resolution, two-dimensional primary x-ray image of said subject at said front detector after said scatter x-rays have been substantially eliminated, said image $D_{fPh}$ having a spatial resolution substantially equal to the highest spatial resolution available from said front detector.

41. A method for taking a two-dimensional x-ray image of a subject using a two-dimensional x-ray imaging system, said subject being composed substantially of two materials, $m_A$ and $m_B$, that interact differently with x-rays and having a two-dimensional projection mass density A for said material $m_A$ and a two-dimensional projection mass density B for said material $m_B$, said imaging system including an x-ray source, a beam selection means, and a two-dimensional x-ray detector having a plurality of detection locations arranged in a substantially rectangular matrix with approximately from approximately 32 to approximately 16,384 locations on a side, said subject being between said x-ray source and said detector, said x-ray source being adapted to emit x-rays for passage through said subject, said x-rays having an energy in the range of from approximately 10 keV to approximately 500 keV, said x-rays including primary x-rays having their direction of travel unaltered by interaction with said subject, said x-rays including scatter x-rays having their direction of travel altered by interaction with said subject, said beam selection means having a blocking position wherein passage of substantially all of said scatter x-rays to said detector is blocked and passage of said primary x-rays to said detector is permitted, said beam selection means having a transmissive position wherein passage of substantially all of said primary x-rays and said scatter x-rays to said detector is permitted, and selected detection locations being those of said detection locations receiving only said primary x-rays when said beaming selection means is in said blocking position, said method comprising:

(a) illuminating said subject with said x-rays;

(b) moving said beam selection means to said transmissive position;

(c) acquiring a high-resolution image $I_{fh}$ from said detection locations and processing said image $I_{fh}$ to normalize it and to subtract dark signals, yielding an image $D_{fh}$ which is composed of said primary x-rays and said scatter x-rays;

(d) producing, from said image $D_{fh}$, a low-resolution image $D_{fl}$ representing said selected detection locations;

(e) moving said beam selection means to said blocking position;

(f) acquiring a low-resolution image $I_{rl}$ from said selected detection locations and processing said image $I_{rl}$ to normalize it and to subtract dark signals, yielding an image $D_{rl}$ which is composed of substantially only said primary x-rays;

(g) calculating a low-resolution primary x-ray image $D_{fPl}$ at said detector by multiplying said image $D_{rl}$ by a predetermined constant that is independent of said subject;

(h) calculating a low-resolution scatter x-ray image $D_{fSl}$ of said detector by subtracting said image $D_{fPl}$ from said image $D_{fl}$;

(i) calculating a high-resolution scatter image $D_{fSh}$ by extending said low-resolution scatter image $D_{fSl}$ to the entire image area of said detector through interpolation; and (j) calculating a high-resolution primary x-ray image $D_{fPh}$ at said detector by subtracting said image $D_{fSh}$ from said image $D_{fh}$;

(k) whereby said image $D_{fPh}$ is a high-resolution, two-dimensional primary x-ray image of said subject at said detector after said scatter x-rays have been substantially eliminated, said image $D_{fPh}$ having a spatial resolution substantially equal to the highest spatial resolution available from said detector.

* * * * *